(12) United States Patent
Hughes et al.

(10) Patent No.: US 6,218,596 B1
(45) Date of Patent: Apr. 17, 2001

(54) ENHANCEMENT OF MUSCULATURE IN NON-HUMAN MAMMALS EXPRESSING C-SKI

(75) Inventors: Stephen H. Hughes, Smithsburg; Pramod Sutrave, Frederick; Vernon Pursel, Highland, all of MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 08/202,841

(22) Filed: Feb. 23, 1994

Related U.S. Application Data

(63) Continuation of application No. 07/620,415, filed on Dec. 3, 1990, now abandoned, which is a continuation-in-part of application No. 07/546,449, filed on Jul. 2, 1990, now abandoned, which is a continuation-in-part of application No. 07/373,864, filed on Jun. 30, 1989, now abandoned.

(51) Int. Cl.$^7$ ................................................. A01K 67/027
(52) U.S. Cl. ................................. 800/14; 800/15; 800/17; 800/18
(58) Field of Search .................................. 800/2, DIG. 1, 800/14, 15, 17, 18; 935/111, 63; 435/172.3, 317.1

(56) References Cited

U.S. PATENT DOCUMENTS 4,736,866 * 4/1988 Leder et al. .............................. 800/2

OTHER PUBLICATIONS

Palmiter et al., Proc. Natl. Acad. Sci. 88:478–482 (1991).*
Kappel et al., Curr. Opin. Biotech. 3:548–553 (1992).*
Pursel et al., J. Reprod. Fert. Suppl. 40:235–245 (1990).*
Shamay et al., Transgenic Research 1:124–132 (1992).*
Li et al., J. Virology 57(3): 1065–1072 (1986).*
Wilmut et al., New Scientist, Jul. 7, 1988, pp. 56–59.*
Van Brunt, BioTechnology 6(10): 1149–1154 (1988).*

* cited by examiner

*Primary Examiner*—Deborah Crouch
(74) *Attorney, Agent, or Firm*—Townsend and Townsend and Crew LLP

(57) ABSTRACT

The present invention relates to DNA segments encoding chicken c-ski protein, to DNA constructs comprising the DNA segments and to cells transformed therewith. The present invention further relates to non-human transgenic mammals having increased muscle size and/or reduced fat. In addition, the present invention relates to methods of stimulating muscle growth and preventing degeneration of muscle, and to methods of treating muscle degenerative diseases and obesity.

13 Claims, 22 Drawing Sheets

(2 of 22 Drawing Sheet(s) Filed in Color)

```
   TC CTC GTC GTC TGT GGA TTG CTA AAC CTG AGT GGG AAG      38
GGG GGG GAA AAA AAA AAG GGT GGG TTG TTG TTT TGT TTA      77
AAA AAA GAA AAA ATC CCT TAA                              98

GTG GAT TTG TAC CAG CGT GGA AGA TAA CTG GGG ATT TTT     137
GTT GTT TGT TTT GGG AAT AGA AAC TAA AAA ATG GAG ACT     176
                                            Met Glu Thr   3
GTA AGT AGA AGC AGC TTC CAG                             197
Val Ser Arg Ser Ser Phe Gln                              10

CCT CAT CCA GGA CTG CAG AAG ACC TTG GAA CAG TTT CAT     236
Pro His Pro Gly Leu Gln Lys Thr Leu Glu Gln Phe His      23
CTG AGC TCT ATG AGC TCC CTG GGT GGC CCT GCT GCT TTC     275
Leu Ser Ser Met Ser Ser Leu Gly Gly Pro Ala Ala Phe      36
TCA GCG CGA TGG GCA CAG GAG                             296
Ser Ala Arg Trp Ala Gln Glu                              43

ATG TAC AAG AAA GAC AAT GGC AAA GAC CCA GCG GAA CCT     335
Met Tyr Lys Lys Asp Asn Gly Lys Asp Pro Ala Glu Pro      56
GTA CTG CAT CTG CCC CCT ATC CAG CCC CCG GTG ATG         374
Val Leu His Leu Pro Pro Ile Gln Pro Pro Pro Val Met      69
CCT GGT CCC TTC TTC ATG CCC                             395
Pro Gly Pro Phe Phe Met Pro                              76

TCG GAC AGA TCC ACT GAG AGG TGC GAG ACC ATC CTG GAA     434
Ser Asp Arg Ser Thr Glu Arg Cys Glu Thr Ile Leu Glu      89
GGG GAA ACC ATC TCC TGC TTC GTG GTG GGT GGG GAA AAG     473
Gly Glu Thr Ile Ser Cys Phe Val Val Gly Gly Glu Lys     102
CGC CTT TGC TTG CCC CAG ATC                             494
Arg Leu Cys Leu Pro Gln Ile                             109

CTG AAC TCG GTG CTC AGG GAC TTC TCC CTG CAG CAG ATC     533
Leu Asn Ser Val Leu Arg Asp Phe Ser Leu Gln Gln Ile     122
AAT TCG GTG TGC GAT GAG CTA CAC ATT TAC TGC TCC AGA     572
Asn Ser Val Cys Asp Glu Leu His Ile Tyr Cys Ser Arg     135
TGC ACC GCT GAC CAG CTG GAG                             593
Cys Thr Ala Asp Gln Leu Glu                             142

ATC CTC AAA GTC ATG GGC ATC TTG CCC TTC TCT GCC CCC     632
Ile Leu Lys Val Met Gly Ile Leu Pro Phe Ser Ala Pro     155
TCC TGC GGG CTG ATC ACT AAA ACT GAT GCT GAG AGG CTT     671
Ser Cys Gly Leu Ile Thr Lys Thr Asp Ala Glu Arg Leu     168
TGC AAT GCC TTG CTT TAT GGT                             692
Cys Asn Ala Leu Leu Tyr Gly                             175
```

*FIG. 2A*

```
GGC ACC TAT CCT CCC CAC TGC AAG AAG GAA TTC TCT AGC      731
Gly Thr Tyr Pro Pro His Cys Lys Lys Glu Phe Ser Ser      188
ACG ATT GAG CTG GAG CTT ACA GAG AAG AGC TTC AAG GTG      770
Thr Ile Glu Leu Glu Leu Thr Glu Lys Ser Phe Lys Val      201
TAC CAC GAG TGC TTT GGG AAG                              791
Tyr His Glu Cys Phe Gly Lys                              208

TGT AAG GGA CTC CTG GTA CCA GAG CTT TAC AGT AAC CCC      830
Cys Lys Gly Leu Leu Val Pro Glu Leu Tyr Ser Asn Pro      221
AGC GCA GCC TGC ATC CAG TGC TTG GAC TGC AGG CTC ATG      869
Ser Ala Ala Cys Ile Gln Cys Leu Asp Cys Arg Leu Met      234
TAC CCG CCT CAC AAA TTT GTG                              890
Tyr Pro Pro His Lys Phe Val                              241

GTC CAC TCT CAC AAA TCC CTG GAA AAC AGG ACT TGC CAC      929
Val His Ser His Lys Ser Leu Glu Asn Arg Thr Cys His      254
TGG GGC TTT GAC TCT GCA AAC TGG AGG TCC TAC ATC CTC      968
Trp Gly Phe Asp Ser Ala Asn Trp Arg Ser Tyr Ile Leu      267
CTT AGC CAG GAT TAC ACT GGG                              989
Leu Ser Gln Asp Tyr Thr Gly                              274

AAA GAG GAG AAA GCT AGG CTG GGC CAG CTC TTA GAT GAA     1028
Lys Glu Glu Lys Ala Arg Leu Gly Gln Leu Leu Asp Glu      287
ATG AAA GAA AAA TTT GAC TAT AAC AAC AAA TAC AAG AGG     1067
Met Lys Glu Lys Phe Asp Tyr Asn Asn Lys Tyr Lys Arg      300
AAA GCC CCC AGG AAC CGT GAG                             1088
Lys Ala Pro Arg Asn Arg Glu                              307

TCT CCT AGA GTT CAG CTC CGC CGG AAC AAA ATG TTC AAG     1127
Ser Pro Arg Val Gln Leu Arg Arg Asn Lys Met Phe Lys      320
ACA ATG CTG TGG GAT CCA GCT GGA GGT TCA GCG GTA CTG     1166
Thr Met Leu Trp Asp Pro Ala Gly Gly Ser Ala Val Leu      333
CAG CGT CAG CCA GAT GGA AAT                             1187
Gln Arg Gln Pro Asp Gly Asn                              340

GAG GTC CCT TCA GAT CCT CCT GCT TCC AAG AAA ACC AAA     1226
Glu Val Pro Ser Asp Pro Pro Ala Ser Lys Lys Thr Lys      353
ATA GAC GAC TCC GCT TCC CAA TCT CCA GCT TCT ACT GAG     1265
Ile Asp Asp Ser Ala Ser Gln Ser Pro Ala Ser Thr Glu      366
AAG GAA AAG CAG TCC AGT TGG                             1286
Lys Glu Lys Gln Ser Ser Trp                              373

TTA CGG TCC TTA TCC AGT TCA TCT AAT AAG AGC ATT GGC     1325
Leu Arg Ser Leu Ser Ser Ser Ser Asn Lys Ser Ile Gly      386
TGT GTC CAT CCC CGT CAG CGT CTC TCA GCT TTC CGG CCC     1364
Cys Val His Pro Arg Gln Arg Leu Ser Ala Phe Arg Pro      399
TGG TCC CCT GCT GTA TCA GCA                             1385
Trp Ser Pro Ala Val Ser Ala                              406
```

*FIG. 2B*

```
AAT GAG AAA GAG CTC TCA ACC CAT CTT CCT GCA TTG ATC    1424
Asn Glu Lys Glu Leu Ser Thr His Leu Pro Ala Leu Ile     419
CGA GAC AGC AGT TTT TAC TCC TAC AAA AGC TTT GAG AAT    1463
Arg Asp Ser Ser Phe Tyr Ser Tyr Lys Ser Phe Glu Asn     432
GCT GTG GCC CCC AAC GTG GCA                            1484
Ala Val Ala Pro Asn Val Ala                             439

CTC GCA CCT CCT GCC CAA CAG AAA GTT GTG AGC AAC CCA    1523
Leu Ala Pro Pro Ala Gln Gln Lys Val Val Ser Asn Pro     452
CCC TGT GCC ACA GTG GTG TCC CGG AGC AGC GAA CCG CCG    1562
Pro Cys Ala Thr Val Val Ser Arg Ser Ser Glu Pro Pro     465
AGC AGC GCT GCG CAG CCA CGG                            1583
Ser Ser Ala Ala Gln Pro Arg                             472

AAA AGA AAA CAT GCT GCA GAA ACC CCG GCT GTC CCA GAG    1622
Lys Arg Lys His Ala Ala Glu Thr Pro Ala Val Pro Glu     485
CCA GTG GCC ACG GTT ACT GCC CCT GAA GAG GAT AAG GAA    1661
Pro Val Ala Thr Val Thr Ala Pro Glu Glu Asp Lys Glu     498
TCA GAA GCA GAA ATT GAA GTA                            1682
Ser Glu Ala Glu Ile Glu Val                             505

GAG ACC AGG GAG GAA TTC ACC TCC TCC TTA TCC TCG CTC    1721
Glu Thr Arg Glu Glu Phe Thr Ser Ser Leu Ser Ser Leu     518
TCC TCC CCA TCC TTT ACT TCA TCC AGC TCT GCA AAG GAC    1760
Ser Ser Pro Ser Phe Thr Ser Ser Ser Ser Ala Lys Asp     531
ATG AGC TCA CCT GGG ATG CAA                            1781
Met Ser Ser Pro Gly Met Gln                             538

GCC CCA GTC CCA GTC AAC AGT TCA TAT GAG GTT GCA GCA    1820
Ala Pro Val Pro Val Asn Ser Ser Tyr Glu Val Ala Ala     551
CAT TCT GAC TCT CAC AGC AGT GGG TTG GAA GCT GAG CTG    1859
His Ser Asp Ser His Ser Ser Gly Leu Glu Ala Glu Leu     564
GAG CAC CTA AGG CAG GCC CTG                            1880
Glu His Leu Arg Gln Ala Leu                             571

GAC AGT GGC CTA GAT ACA AAA GAA GCC AAA GAA AAA TTC    1919
Asp Ser Gly Leu Asp Thr Lys Glu Ala Lys Glu Lys Phe     584
CTC CAT GAA GTT GTT AAA ATG AGA GTG AAG CAG GAA GAG    1958
Leu His Glu Val Val Lys Met Arg Val Lys Gln Glu Glu     597
AAG CTA AAT GCT GCC TTG CAA                            1979
Lys Leu Asn Ala Ala Leu Gln                             604

GCC AAA CGC AGC CTA CAT CAG GAG CTG GAG TTC CTC AGA    2018
Ala Lys Arg Ser Leu His Gln Glu Leu Glu Phe Leu Arg     617
GTG GCA AAG AAG GAG AAA CTG AGA GAA GCA ACG GAG GCA    2057
Val Ala Lys Lys Glu Lys Leu Arg Glu Ala Thr Glu Ala     630
AAA CGC AAC TTA AGG AAA GAG                            2078
Lys Arg Asn Leu Arg Lys Glu                             637
```

FIG. 2C

```
ATT GAG CGT CTG AGA GCT GAG AAT GAG AAG AAA ATG AAG         2117
Ile Glu Arg Leu Arg Ala Glu Asn Glu Lys Lys Met Lys          650
GAA GCA AAC GAG TCT CGG ATA CGG CTA AAG AGG GAA CTG         2156
Glu Ala Asn Glu Ser Arg Ile Arg Leu Lys Arg Glu Leu          663
GAA CAA GCC AGG CAG ATC CGG                                 2177
Glu Gln Ala Arg Gln Ile Arg                                  670

GTT TGC GAC AAG GGT TGT GAA GCT GGC AGG CTT CGG GCC         2216
Val Cys Asp Lys Gly Cys Glu Ala Gly Arg Leu Arg Ala          683
AAG TAC TCT GCC CAG ATT GAG GAC CTA CAG GTT AAG CTT         2255
Lys Tyr Ser Ala Gln Ile Glu Asp Leu Gln Val Lys Leu          696
CAG CAT GCA GAG GCT GAC AGG                                 2276
Gln His Ala Glu Ala Asp Arg                                  703

GAG CAG CTC CGA GCT GAC CTG ATG CAT GAG AGG GAG GCT         2315
Glu Gln Leu Arg Ala Asp Leu Met His Glu Arg Glu Ala          716
CGA GAA CAC TTG GAA AAA GTA GTC AAG GAA CTT CAG GAA         2354
Arg Glu His Leu Glu Lys Val Val Lys Glu Leu Gln Glu          729
CAG CTG TGG CCT AAA TCA AGC                                 2375
Gln Leu Trp Pro Lys Ser Ser                                  736

AGT CAA TCC AGC AGT GAA AAC ACA ACG AGC AAC ATG GAG         2414
Ser Gln Ser Ser Ser Glu Asn Thr Thr Ser Asn Met Glu          749
AAT TAA ACC ACG TCG TCT AAT ACA ACA GAA TGA CAT ATA         2453
Asn End                                                      751
TGC ACA GTA AGG GAG GAT GGG                                 2474

TGGGGTACGT GTGTAAGTGC ATGTGTGAGT AGTTGTGTCT                 2514
TAACACACAG ATCTAGGAAT ATGGATTCTT ATTAGTTGGA                 2554
AGGCAAATGT TACTCTTTAT AACAGAAGCA CTGAATTACG                 2594

CCTCTTTTTT TTTCCAATCC ATATAGCACA ACATCTTACT                 2634
GTGCCTATAA AACACAAATG TGTTTATAAA CAAAATACTT                 2674
TTAAGTCCAC AGCAAATTTT CTACTGGCAA ACTCCAAGCA                 2714

AGCAGCATCC TCCAACTAGA ATCAGAGTAA AAGGCAAGCA                 2754
TGGCAGTGTT TTCATGTTGC CCTTCTGCCT GTCGGAACAT                 2794
TTTGGAATTT AAAAACAAAC TTTTCTTATA AGCTATTTAA                 2834

AGTAATTCAT TACACAGACT TGGTATTAAA AAAAATTAAC                 2874
AAGATTTTTT ATAACGAACC TTTAAAAGCA AAACAAAAAC                 2914
CTTCGATGCA CAATTTTTAC GACTTGTTAA AGGCTTTGGG                 2954

ATTCTTACTG CAGAAGCCCT TTGGTGATGA TGCCATTTCA                 2994
TTAGCAGTTT TTTTTAATCC TGTCCTGTGG TTGTATGAGA                 3034
ATTTCAGAGT GCTTTTCAAA GTTGATTTTT TTCCTTAGAA                 3074
```

FIG. 2D

| | |
|---|---|
| ACAATCACCT TCATTTCCTG TCCTGAACAC AAGAAGAAAG | 3114 |
| GAAGATGCAG GACTGTAAGG GCGTGGGGGA GGGCAGGAAG | 3154 |
| AGAAGATGGA CGCTTTGGAA TTATAAACCC AGCCTTACAG | 3194 |
| ACTTCAGTGT TTCAAATCAC GCCATGTTTT CTAAAGACGT | 3234 |
| CTTCATTAAT CGATGTGTTC AAAAGACTCA CTTCATCCAA | 3274 |
| GAGCACTTCA GCTTTAGGAA AAGAAAGAAG GAAGTAAAGG | 3314 |
| AAGGAAATGG ATGACCTGTT AAGTTGGTTG AGAAATAAAG | 3354 |
| CAGAAGATGT GTTTTGAAGT CATTCTGAAA TCTTCGCGTC | 3394 |
| AGCTTTCAGT TCTCTGGAAA ACTCATCTTT GTTGCACCAT | 3434 |
| CTTACCATAG AATTCAGTAT TTACCTACTT CTATTCTGAA | 3474 |
| CTGTTTGTCA GGATTTCTGT GCCCAAGGAG AGTGCAACAC | 3514 |
| CGCATTATTG GATACTACAG AAAAGAAAAA CCACGTTTTT | 3554 |
| GCTGCTGTGA ATAAGCCTAC ATCTTTTTTA AAAGAAAAAC | 3594 |
| TTCTGTTTTT AAGAATAGAA ATTACTTTAA TTTTGGGATC | 3634 |
| CGAGCCGCAG CCCTGGAATA GAAATGCAGC CTACCATCAC | 3674 |
| TCTGTCTTAC TACCATTGTT AGCGTCGTCG TTCATTTTTT | 3714 |
| TTTAAACTGC ACTTTGTCAG AACCTCACTC TGCATTTTAT | 3754 |
| TCCATATTTT GGAAGTTTAC AAGTTCAGCA TTCTCGATTC | 3794 |
| TGCTCTGCAG ATGTTAAAAT CATCACCACC ATTTTCCACC | 3834 |
| ACGCGACACC TCGGCCGTCA TTTCCATGTA TGCAAAAGAA | 3874 |
| GAACTCAGTG GGTACAGAAT GCTACCAAAT ACAAAGGCAG | 3914 |
| CAGAGCAGCG TGCTGCTGGT TGGGTTTCAC AGCTGCGCTG | 3954 |
| CACGGCTGTG GCTGTCGAGG CTGGGAAGTG CTCAAATACA | 3994 |
| GTTGGTGCTT TACTGAATGA GAGAGGAGTT ATTTTCACCC | 4034 |
| ACACACACTC ACCTCTGATA CACTCAAGCT CAGTGAAAAG | 4074 |
| TTGATCTGGG GCTGCAGTTG TGCCTTCCAG CTCATTTTTC | 4114 |
| CTCTCAGCAT CTTCTATAGG CAATGCTGAC ACTTTTTTTT | 4154 |
| TAAACCTTAA AGAATAAAAA G | 4175 |

*FIG. 2E*

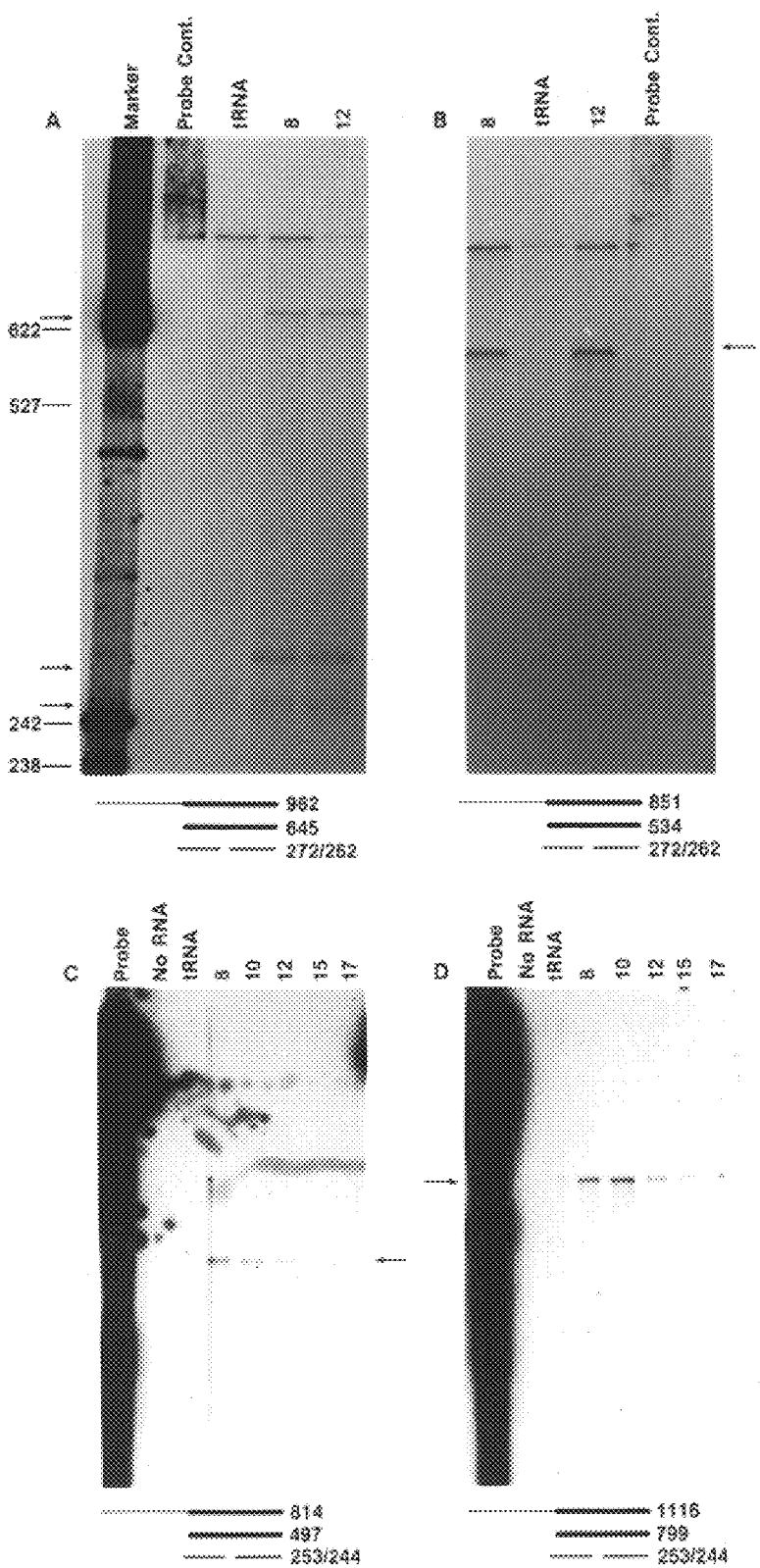
FIG. Cont.

```
ALV     GAGA GGAACAG G TT A CATCTGAGC A A
c-ski   CCTT GGAACAG T TT - CATCTGAGC T C
```

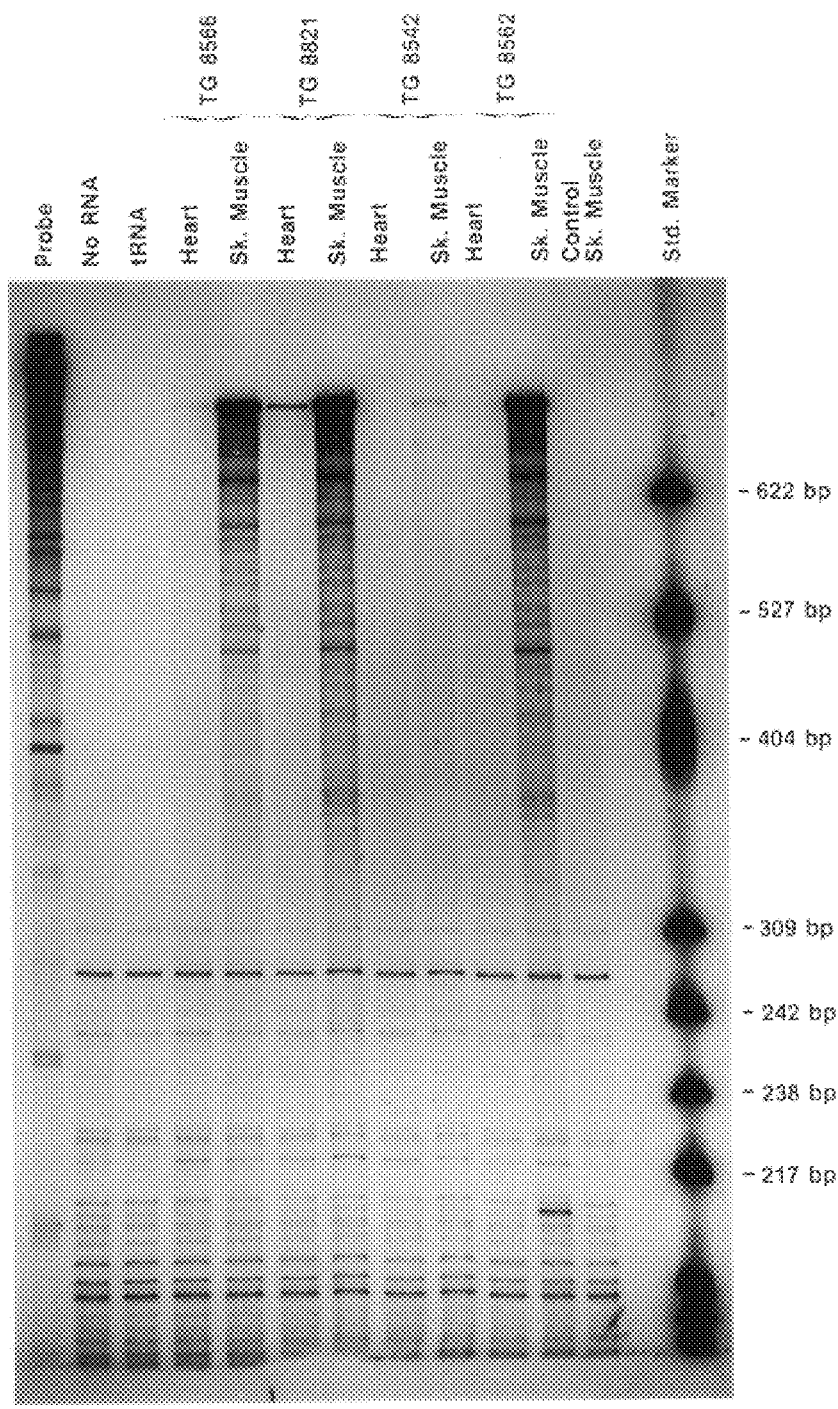
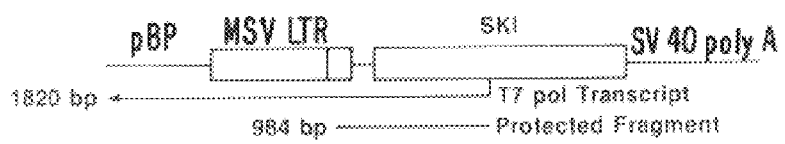
FIG. 9.

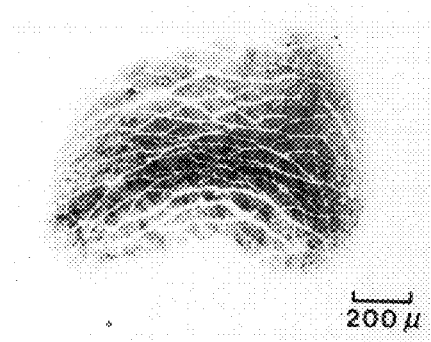
FIG. IIA.
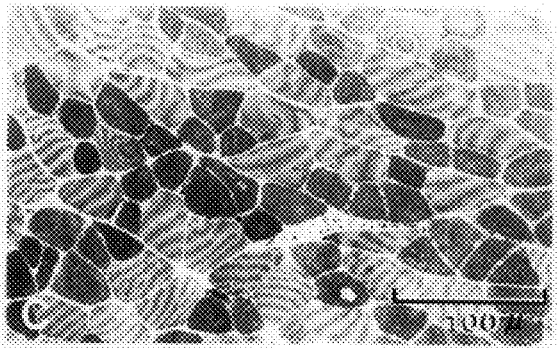
FIG. IIC.
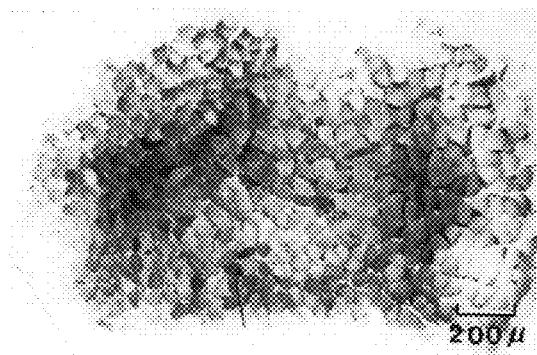
FIG. IIB.
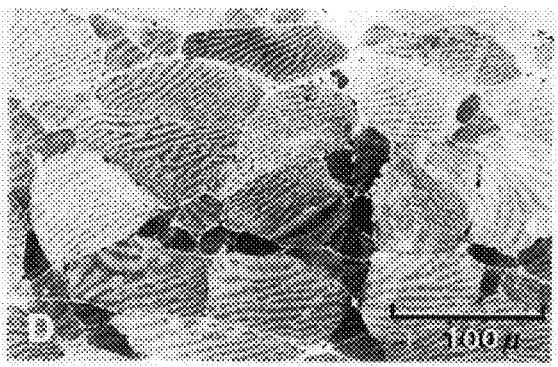
FIG. IID.

ENHANCEMENT OF MUSCULATURE IN NON-HUMAN MAMMALS EXPRESSING C-SKI

This is a Continuation of application Ser. No. 07/620,415, filed Dec. 3, 1990, now abandoned which was a Continuation-in-Part of Ser. No. 07/546,449 filed Jul. 2, 1990, now abandoned, which was a Continuation-in-Part of Ser. No. 07/373,864, filed Jun. 30, 1989, now abandoned.

BACKGROUND OF THE INVENTION

1. Field of the Invention

The present invention relates the c-ski gene. In particular, the present invention relates to DNA segments encoding chicken c-ski protein, to DNA constructs comprising the DNA segments and to cells transformed therewith. The present invention further relates to animals having increased muscle size and/or reduced amounts of fat.

2. Background Information

Viruses that contain the v-ski oncogene are not only capable of causing morphological transformation in vitro, but also can induce myogenic differentiation (Stavnezer et al., 1981, J. Virol. 39, 920–934; Li et al., 1986, J. Virol. 57, 1065–1072; Stavnezer et al., 1986, J. Virol. 57, 1073–1083; Colmenares and Stavnezer, 1989, Cell 59, 293–303). Viruses that carry and express c-ski cDNAs also induce foci and myogenic differentiation (Sutrave et al., 1990, Mol. Cell. Biol. 10, 3137–3144). This suggests the possibility that the ski oncogene is bifunctional since the two known functions of ski, transformation and differentiation, would appear to be contradictory properties. Using a v-ski probe, genomic clones for c-ski have been isolated and partially sequenced (Stavnezer et al., 1989, Mol. Cell. Biol. 9, 4038–4045). Comparisons of the properties of two forms of c-ski that are related by alternative splicing, and of several v-ski and c-ski deletion mutants have shown that the portions of ski required for transformation and differentiation are quite similar. These results suggest that the ability of c-ski and v-ski to cause transformation and induce differentiation may be related aspects of a single property of ski rather than two separate functions.

Relatively little is known about the biochemical functions of the ski proteins. All of the biologically active forms of c-ski and v-ski that have been studied are localized primarily in the nucleus (Barkas et al., 1986, Virology 151, 131–138; Sutrave et al., 1990, Mol. Cell. Biol. 10, 3137–3144). When the c-ski proteins are overexpressed in chicken cells, different forms of c-ski differ in their subnuclear localization; however, the significance of these differences, if any, is as yet unclear. when chromatin condenses for cell division, the over-expressed c-ski proteins are associated with the condensed chromatin (Sutrave et al., 1990, Mol. Cell. Biol. 10, 3137–3144). Biochemical studies have also shown that at least one form of c-ski can bind to DNA in the presence of other proteins (Nagase et al., 1990, Nucl. Acids Res. 18, 337–343).

None of the available data make it possible to infer the normal function of c-ski either in terms of its role in growth and development (if any) or to have any direct insight into its mode of action.

SUMMARY OF THE INVENTION

It is an object of the present invention to provide an isolated and characterized c-ski cDNA.

It is another object of the present invention to provide a gene that increases the muscle size in animals.

It is another object of the present invention to provide domestic livestock with increased muscle size and decreased fat tissue.

It is a further object of the present invention to provide a treatment for patients suffering from serious muscle injury or muscle degenerative diseases.

It is a further object of the present invention to provide a treatment for patients suffering from obesity.

Various other objects and advantages of the present invention will be apparent from the drawings and the following description of the invention.

In one embodiment, the present invention relates to a DNA segment encoding a chicken c-ski protein or a DNA fragment complementary to said segment.

In another embodiment, the present invention relates to a DNA construct comprising a DNA segment encoding a chicken c-ski protein and a vector. In a further embodiment, the present invention relates to a DNA construct comprising a DNA segment encoding a truncated chicken c-ski protein having the function of c-ski and a vector. The present invention also relates to host cells stably transformed with either one of the two DNA constructs described above, in a manner allowing expression of the protein encoded in the construct.

In yet another embodiment, the present invention relates to a animal having increased muscle size, all of whose cells contain a DNA construct comprising a DNA segment encoding a ski protein and a vector, introduced into the animal, or an ancestor of the animal. The DNA segment may encode the entire protein or a truncated version thereof.

In further embodiment, the present invention relates to an animal having increased muscle size and/or reduced fat, all of whose cells contain a DNA construct comprising a DNA segment encoding a truncated ski protein having the function of ski and a vector, introduced into the animal, or an ancestor of the animal.

In another embodiment, the present invention relates to a method of stimulating muscle growth or preventing muscle degeneration comprising delivering a DNA construct of the present invention to the muscle under conditions such that the protein of the construct is expressed and muscle growth induced.

In a further embodiment, the present invention relates to a method of treating a muscle degenerative disease comprising delivering a DNA construct of the present invention to the effected muscle under conditions such that the protein of the construct is expressed and treatment effected.

BRIEF DESCRIPTION OF THE DRAWINGS

The file of this patent contains at least one drawing executed in color. Copies of this patent with color drawings are provided to the Patent and Trademark Office with payment of the necessary fee.

FIG. 2. Complete coding sequence and the potential coding region of a cDNA of the FB29 type (cDNA=SEQ ID NO:1; amino acids=SEQ ID NO:2). This assumes that the 5' end sequences of the FB29 are similar to the 5' ends of the FB28 and CEL clones. ↑ indicates the site where FB28 and CEL diverge. The 25 bases found only in the CEL clones are not shown. ↓ indicates the boundaries of v-ski. The exon boundaries are numbered and the alternately spliced exons are boxed. The single base and amino acid change between c-ski and v-ski is also boxed with a dashed line. The translation termination codon is boxed in thick lines. The potential polyadenylation signals are densely underlined. The AT rich region containing ATTTA sequences that might be involved in mRNA stability is underlined with dashed lines.

Figure 1:
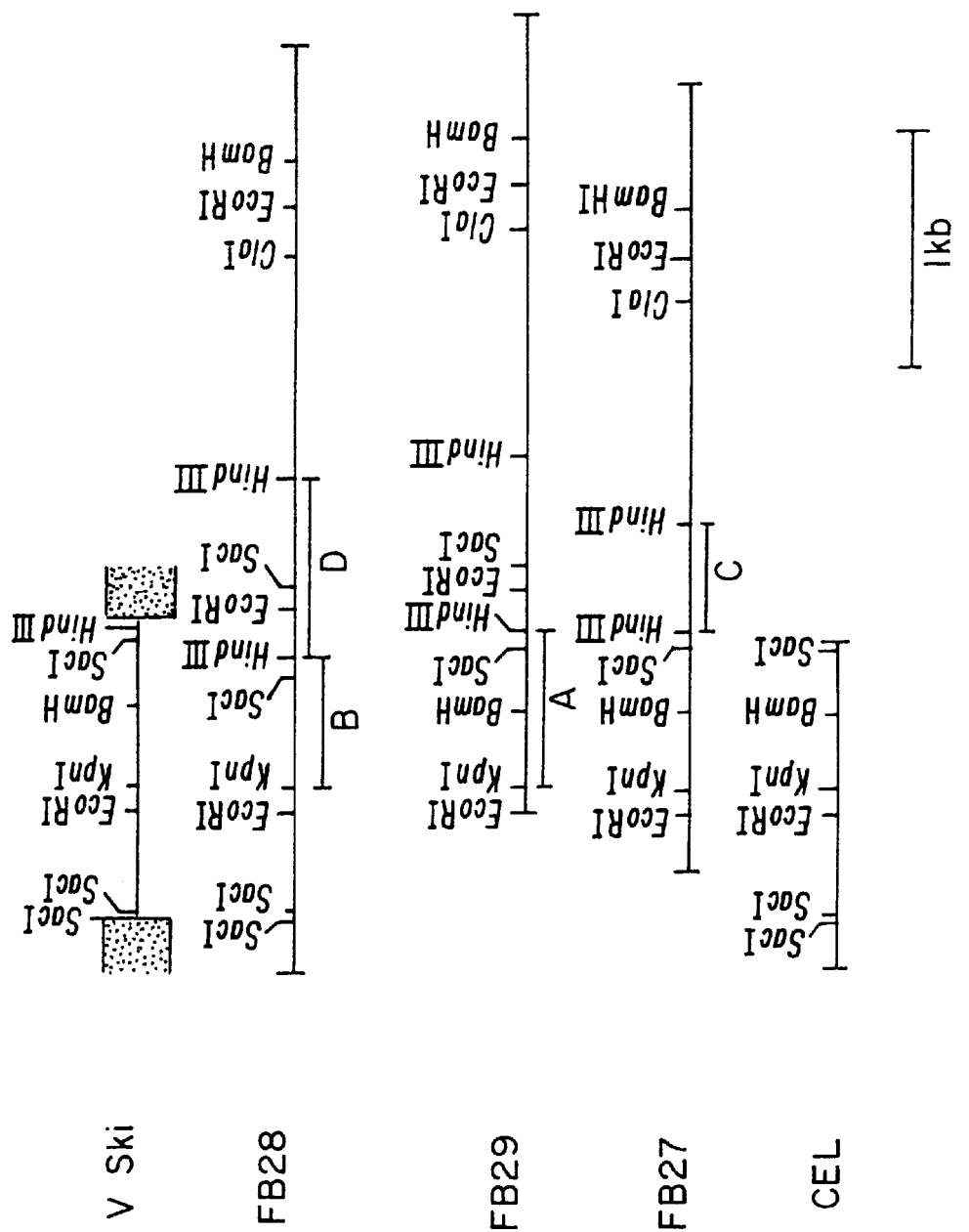
FIG. 1. The Structure of the c-ski cDNA clones. The lengths of the cDNAs are drawn to scale and the restriction sites indicated. v-ski is shown for comparison. The dotted boxes in v-ski represent the gag region of the gag-ski fusion in the acutely transforming virus SKV. A, B, C and D represent the regions used for generating single-strand probes for S1 nuclease protection analysis.

Probe A (see FIG. 1) contains a KpnI-HindIII fragment of the FB27/29 type. This probe produced a fragment of 645 base pairs (bp) and two smaller fragments of 262 and 272 bp, shown by arrows.

Probe B (see FIG. 1) contains a KpnI-HindIII fragment of the FB28 type. This probe produced a fragment of 534 bp as shown by the arrows. Smaller fragments were not detected.

Probe C (see FIG. 1) contains a 497-bp HindIII fragment of the FB27 type linked to M13 sequences. The probe yielded a 497-bp fragment and two smaller fragments of 243/254. Only the 479-bp fragment is marked by an arrow.

Probe D (see FIG. 1) is 1116 bp in length containing a HindIII fragment of FB28/29 type. Probe D produced a 799-bp fragment which is marked by an arrow.

Figures 5, 6:
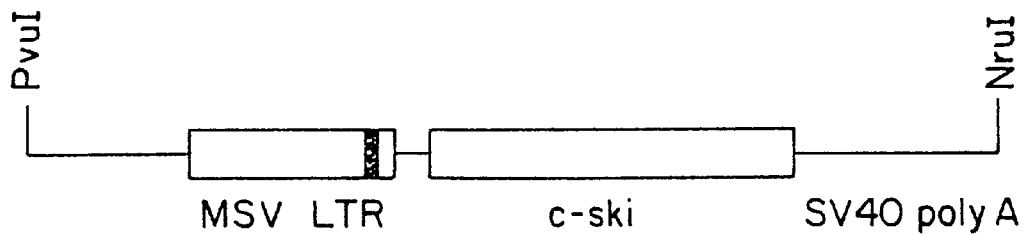

FIG. 5. Sequence homology between c-ski and the p19 region of gag from avian leukosis virus. The c-ski sequences are from positions 218 to 242 (SEQ ID NO:4) and the p19 sequence of gag region are from positions 633 to 658 (SEQ ID NO:3). The homologous regions are boxed.

FIG. 6. The c-ski expression cassette. The PvuI to NruI segment shown in the drawing was isolated by gel electrophoresis following double digestion of the plasmid. The linear DNA was used to create the transgenic mice by microinjection of fertilized eggs.

Figure 7:
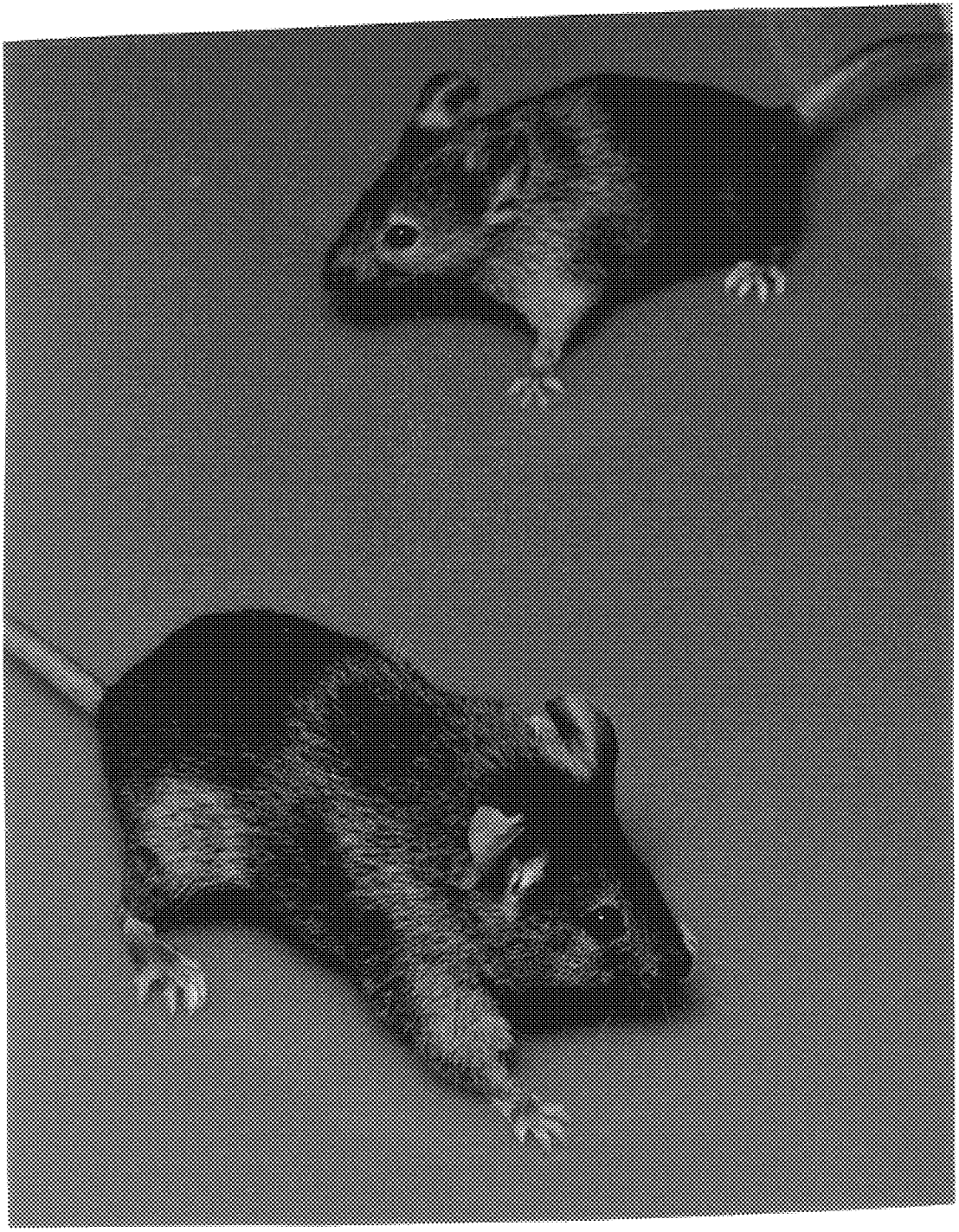

FIG. 7. A transgenic mouse that expresses c-ski and a normal litter mate. The c-ski transgene appears to segregate normally in crosses. The photograph shows a heterozygous mouse that displays the muscular phenotype (foreground) and a DNA-negative litter mate. Double blind DNA analyses confirmed that the muscular phenotype segregates with the transgene.

Figure 8A:
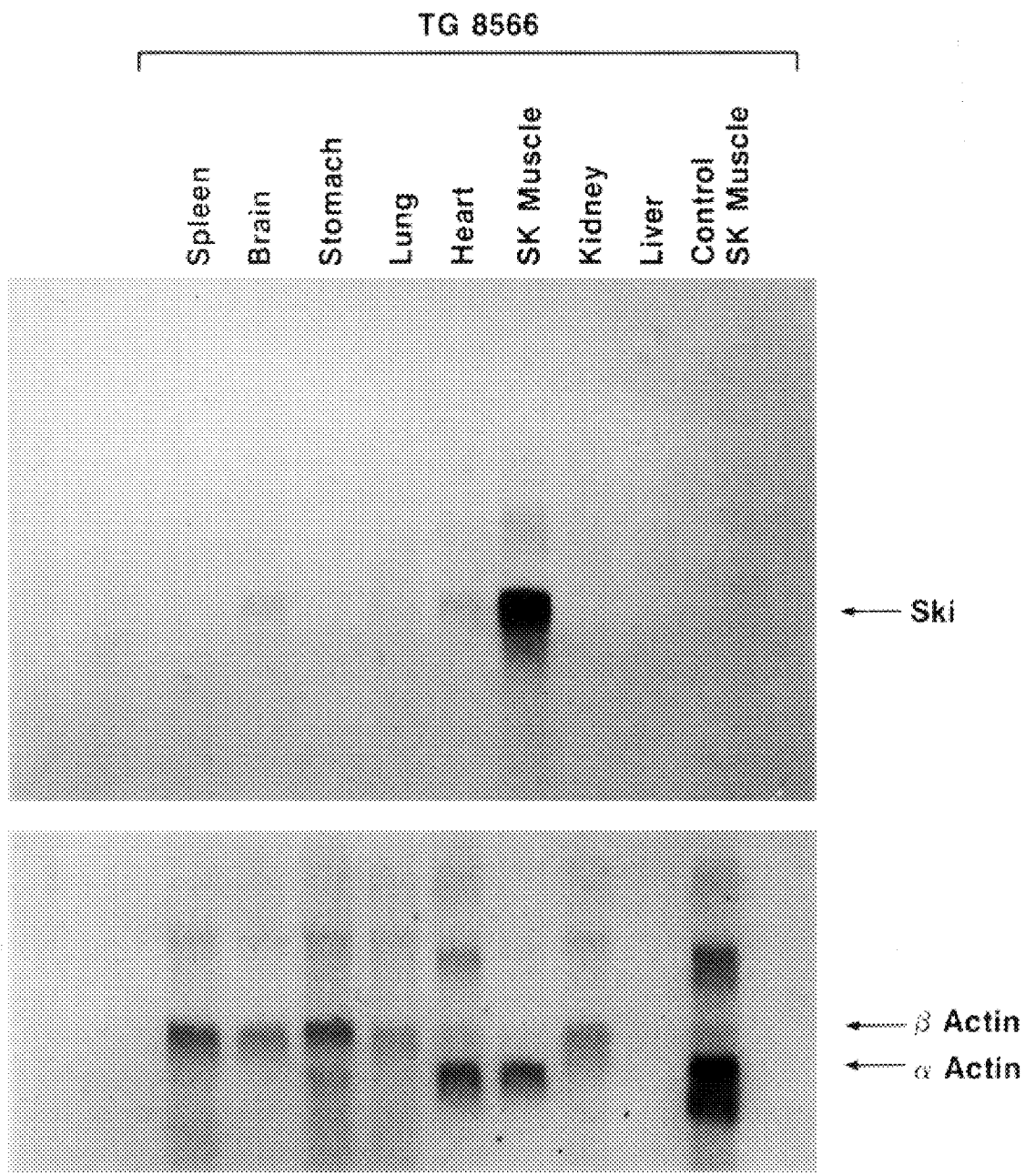
Figure 8B:
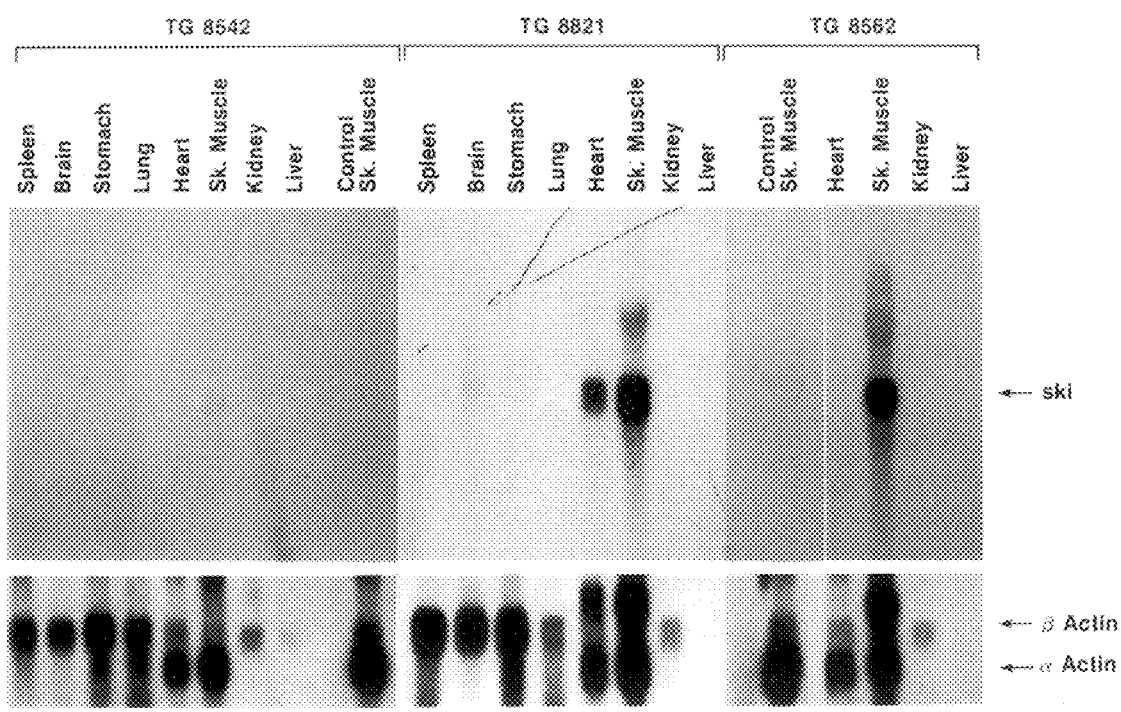

FIG. 8(A–B). Northern transfer analysis of transgene expression. Panel A shows the analysis of RNA isolated from various tissues of a mouse of the line TG 8566. The upper part of the panel shows an autoradiogram after hybridization with chicken c-ski. The expected position of migration of the c-ski message appropriately transcribed from the transgene is 2.5 kb. The position corresponding to 2.5 kb is marked (ski). The lower panel shows an autoradiogram from the same filter following hybridization to a chicken β-actin cDNA. The β-actin cDNA will hybridize not only with β-actin mRNA but also with other actin messages. The expected position of migration of both β-actin and α-actin mRNAs are indicated on the right of the panel. Panel B. The autoradiograms shown in panel B are similar to those shown in panel A except that the RNAs derive from three other transgenic lines. The lines used to prepare the RNAs are indicated at the top of the figure. The filters shown in panel B were done at the same time; those in panel A were done on a different day.

FIG. 9. RNase protection of RNA from the transgene. The top of the figure shows an autoradiogram of the gel. The first lane contains the antisense RNA probe, without RNase digestion. The next two lanes show the results of digestion following hybridization of the probe either without added RNA or with tRNA. The next eight lanes show the results of hybridization to RNA isolated either from the hearts (heart) or the skeletal muscle (SK muscle) of the four transgenic lines. The next lanes show the results of hybridizing the probe to RNA from skeletal muscle of a mouse that does not carry the transgene (control SK muscle). The last lane contains molecular weight markers. Below the autoradiogram is a diagram that shows a drawing of the MSV LTR c-ski expression cassette in relation to the antisense RNA probe. The T7 transcript begins in the middle of the c-ski coding region and goes entirely through the MSV LTR into adjacent sequences that derive from pBR322 (marked pBR). If the transcripts deriving from the transgene initiate appropriately, then a fragment of 984 bases should be protected.

Figure 10:
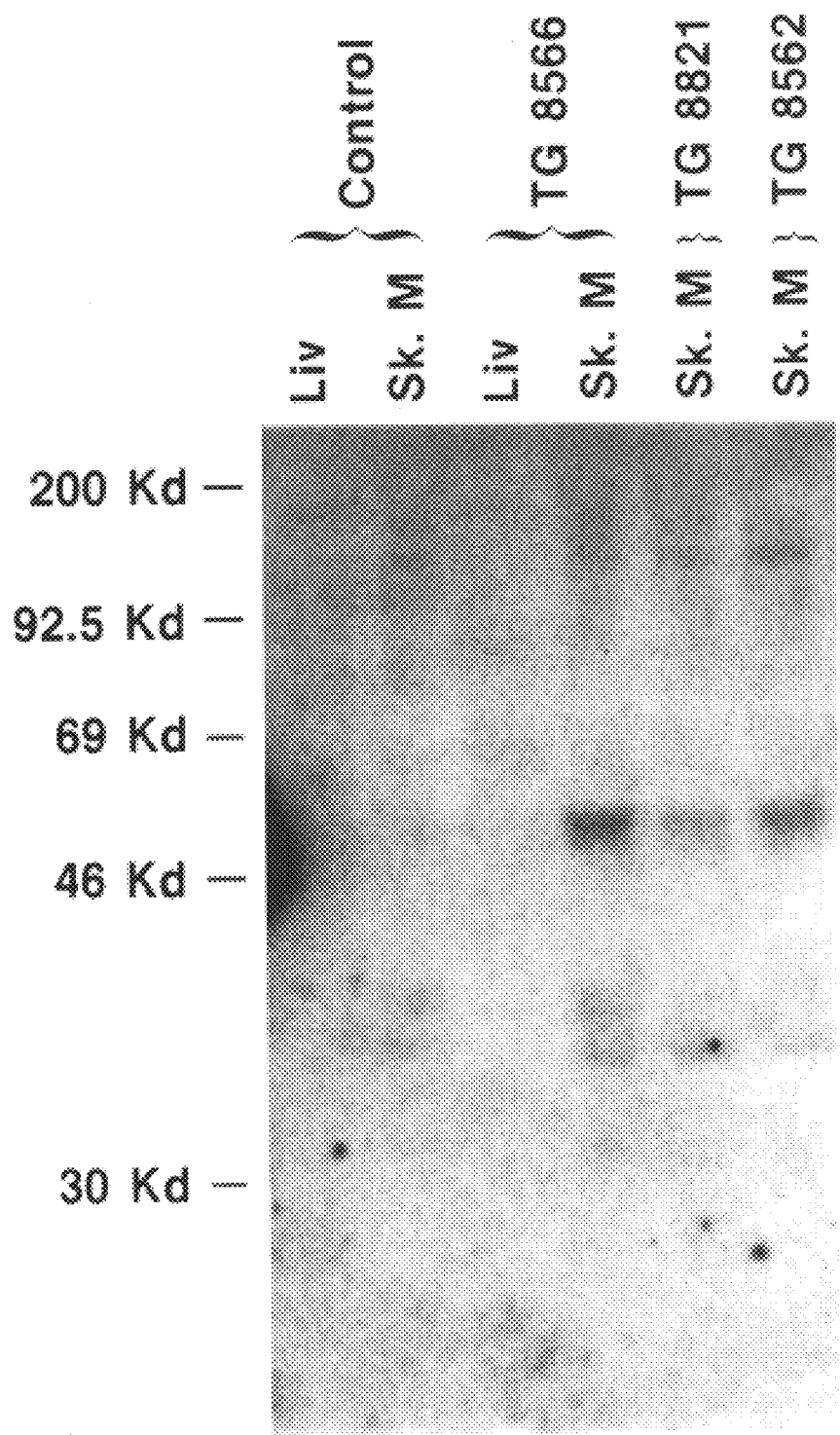

FIG. 10. chicken c-ski protein expression in transgenic mice. Extracts were made from the liver (Liv) or skeletal muscle (Sk.M) of control mice (control) or mice carrying and expressing the c-ski transgene. The positions of migration of radioactively labeled molecular weight standards are shown to the left of the figure.

FIG. 11(A–D). Cross sections made precisely through the middle of the plantaris muscle: (a) from control mouse and (b) from a mouse of line TG 8566. Both illustrations are at the same magnification, the size marker is 200μ. (c) Higher power illustration from the plantaris of control and (d) from the plantaris of an affected mouse. Size markers in (c) and (d) are 100μ.

Figure 12A:
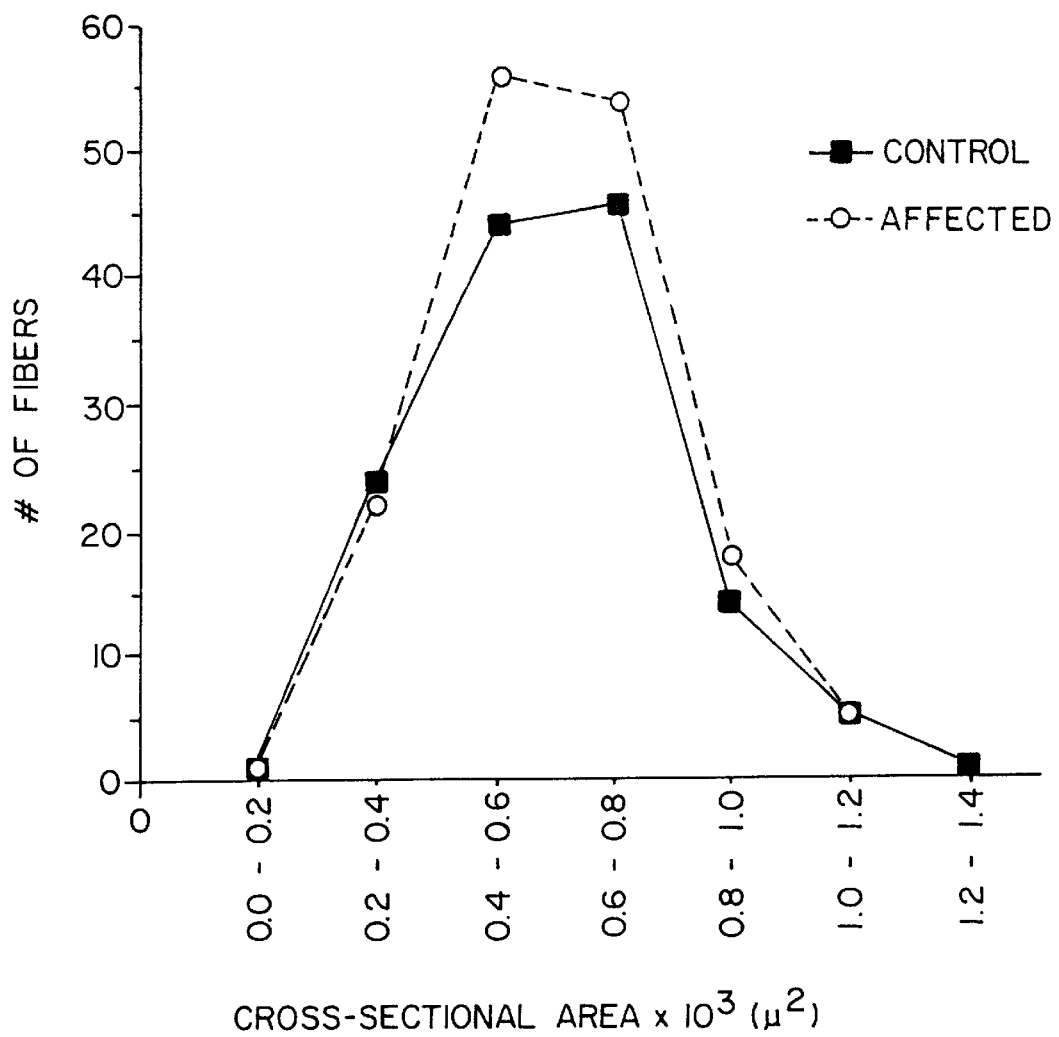
Figure 12B:
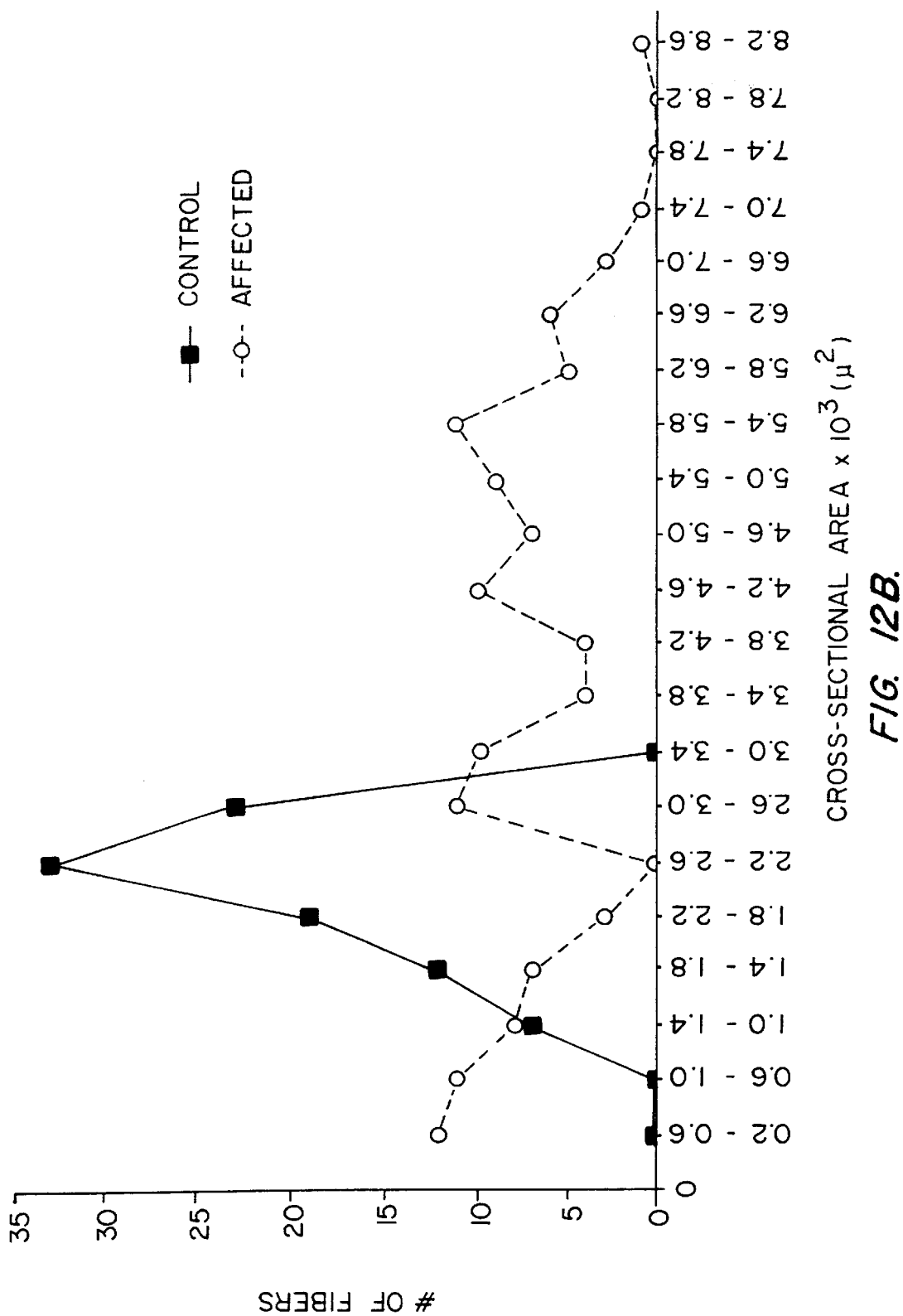

FIG. 12(A–B). Distribution of fiber diameters in selected muscles from normal and transgenic Mice Panel A. The diaphragm appears normal in transgenic mice that express c-ski. A diaphragm from a mouse that has the muscular phenotype (TG 8566) and a diaphragm from a normal control mouse were sectioned and the number of individual muscle fibers of a given cross-sectional area tallied. Panel B. The anterior tibial muscle is grossly enlarged in mice from the line TG 8566. Transverse sections were prepared from both a transgenic mouse and a control mouse. The number of fibers of each given cross-sectional area were tallied. This muscle is composed of two distinct types of fibers, some of which are smaller, others larger, than the fibers found in the controls (see also FIG. 11).

Figure 13:
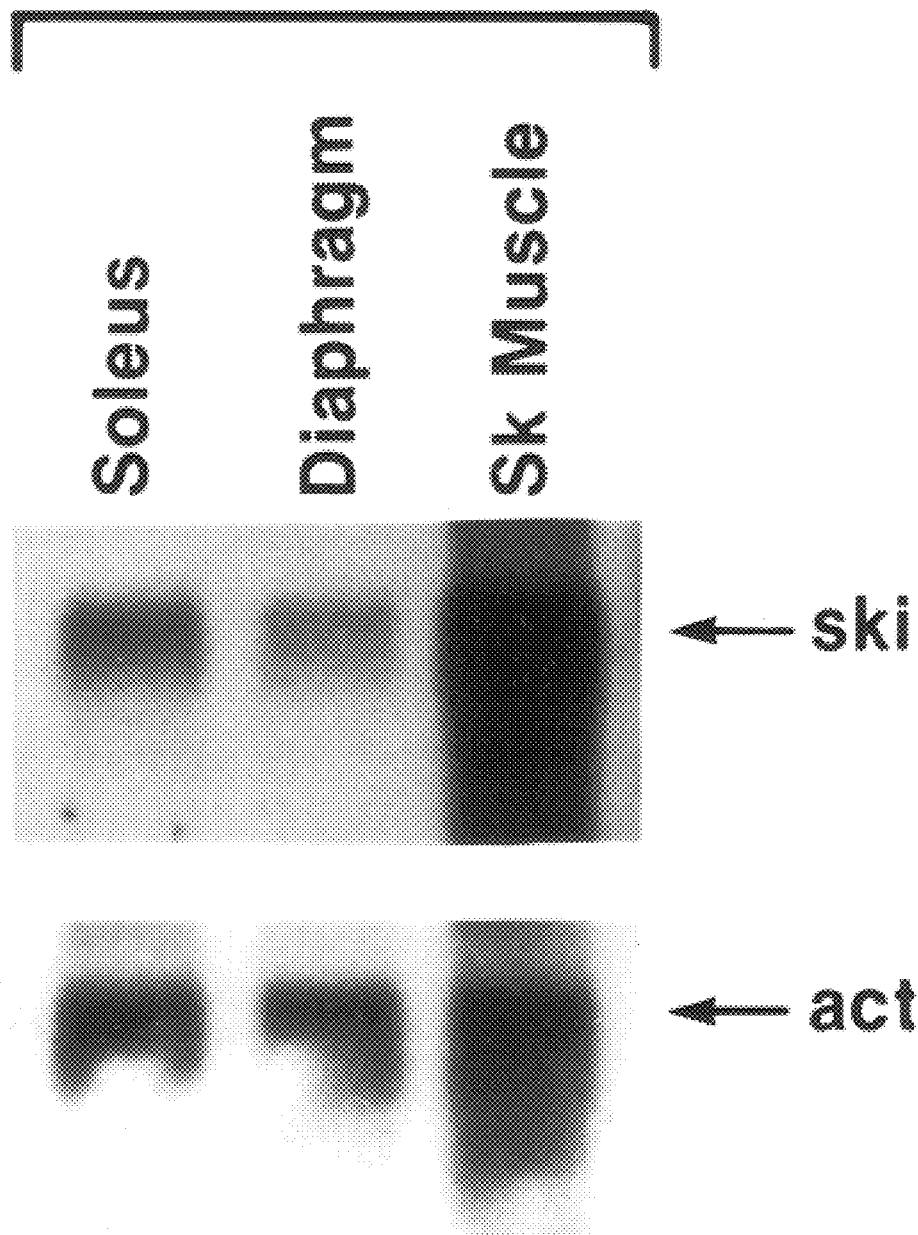

FIG. 13. Transgene expression in specific muscles from TG 8566. 20 μg of total RNA was fractionated by electrophoresis and transferred to nitrocellulose membranes. The transfers were first probed with chicken c-ski, then the filters were stripped and reprobed with a chicken β-actin cDNA (Cleveland et al., 1980, Cell 20, 95–105). The RNA was isolated from the diaphragm, the soleus, or from bulk skeletal muscle (sk muscle).

FIG. 14(A–D). Immunofluorescence staining of sections made through the middle of the Rhomboideus capitis muscle of an affected mouse (transgenic line 8566). (a) staining with monoclonal antibody NOQ7 5 4D, specific for slow MHC. Slow fibers are not hypertrophied. (b) staining with monoclonal antibody SC 711 specific for IIa MHC. IIa fibers are not hypertrophied. (c) is with monoclonal antibody 2G3 which reacts with all fast MHC isoforms. All hypertrophied fibers stain with this antibody. (d) is with m/a BF-F3 specific for IIb MHC. Many, but not all, hypertrophied fibers stain. Magnification×230.

Figure 15A:
Figure 15B:

FIG. 15(A–B). Transgenic pigs that contain c-ski and control pigs. (A) The photograph shows a transgenic pig (3-0102) (left) that displays the muscular phenotype of the shoulders and a control pig (right). (B) The photograph shows transgenic pigs that display the muscular phenotype of the rear quarters (3-0503 (left) and 3-0202 (second from left)) and a control pig (3-0203, third from left).

DETAILED DESCRIPTION OF THE INVENTION

The present invention relates to a DNA segment encoding all, or a unique portion, of a chicken c-ski protein. The DNA segment may encode one of several chicken c-ski proteins, for example, FB29, FB28 and FB27. A "unique portion" as used herein is defined as consisting of at least five (or six) amino acids or correspondingly, at least 15 (or 18) nucleotides. The invention also relates to DNA constructs containing such DNA segments and to cells transformed therewith.

The present invention relates to DNA segments that encode the amino acid sequence of exon 6 given in FIG. 2 or the amino acid sequence of exon 7 given in FIG. 2. The present invention also relates to DNA segments that in addition to exon 7 further comprise at least four exons selected from the group consisting of: exon 1, exon 2, exon 3, exon 4, exon 5 or exon 6, given in FIG. 2. Examples of such DNA segments include FB29, FB28, and FB27.

DNA segments to which the invention relates also include those encoding substantially the same proteins as those encoded in the exons of FIG. 2 which includes, for example, allelic forms of the FIG. 2 amino acid sequences. The invention also relates to DNA fragments complementary to such sequences. A unique portion of the DNA segment or the complementary fragment thereof of the present invention can be used as probes for detecting the presence of its complementary strand in a DNA or RNA sample.

The present invention further relates to DNA constructs and to host cells transformed therewith. In one embodiment, the DNA constructs of the present invention comprise a DNA segment encoding a c-ski protein of the present invention and a vector, for example, pMEX neo. In another embodiment, the DNA constructs comprise a DNA segment encoding a truncated c-ski protein having the function of c-ski (such as, for example, ΔFB29) and a vector (for example, pMEX neo). The DNA construct is suitable for transforming host cells. The host cells can be procaryotic or, preferably, eucaryotic (such as, mammalian).

The present invention further relates to animals, such as, for example, domestic livestock, having increased muscle size and/or reduced fat. The development of such strains of domestic livestock with increased muscles continues to be a major goal of conventional breeding schemes. (Domestic livestock as used herein refers to animals bred for their meat, such as, for example, pigs, chickens, turkeys, ducks, sheep, cows and fish, particularly, trout and catfish).

Introduction of various genes into the germ lines of mice and of some types of domestic livestock is relatively routine to those skilled in the art. The present inventors have produced mice having increased muscle size by introducing a DNA construct comprising ΔFB29 and the pMEX neo vector into fertilized eggs. Resulting founder mice and their offspring have the DNA construct in all their cells, somatic and germ.

Introduction of DNA constructs encoding a ski protein (such as, for example a c-ski protein), into fertilized eggs of animals (such as, by microinjection) results in strains of animals having increased muscle development and decreased fatty tissue. As one skilled in the art will appreciate, the animals with increased muscle size of the present invention can also be produced using DNA encoding a ski protein from various species (chicken being just one such example). Furthermore, animals of the present invention can be produced using a DNA construct encoding proteins related to ski, such as, for example, the sno gene.

The DNA segment ΔFB29 generated by a frameshift mutation results in a truncated protein. However, as one skilled in the art will appreciate, the transgenic animals of the present invention can also be generated by DNA constructs containing DNA segments encoding a full length ski protein, a portion of a ski protein, such as, one or two exons or a biological active deletion derivative, such as, for example, v-ski, which represents a truncated c-ski fused to a viral protein. Further, it is also recognized that the selective expression of the protein in muscle tissue may result from DNA constructs created in vectors other than pMEX neo.

The present invention also relates to a method of stimulating muscle growth and preventing muscle degeneration in an animal, such as for example, a human. A possible treatment for injuries resulting in loss of muscle tissue and neurological injuries resulting in degeneration of the muscle would be to stimulate muscle growth. In the case of lose of muscle this would involve stimulating regrowth of the tissue. Whereas in the case of neurological injuries, the muscle growth would need to be rendered independent of the missing nerve stimulus. According to the present invention, muscle growth could be stimulated by delivering a DNA construct encoding a ski protein to the muscle tissue under conditions such that the protein encoded in the construct is expressed. The construct can be targeted and delivered to the muscle using standard methods known to those skilled in the art.

The present invention further relates to a method of treating a muscle degenerative disease such as, for example, muscular dystrophy and amyotrophic lateral sclerosis (also known as Lou Gehrig disease). Treatment would comprise delivering a DNA construct of the present invention to the effected muscle under conditions such that the protein encoded in the construct is expressed and treatment effected.

EXAMPLES

Screening of cDNA Library

Two chicken cDNA libraries were screened with a v-ski probe using standard protocols (Maniatis et al., 1982, Molecular Cloning. A Laboratory Manual. Cold spring Harbor Laboratory, Cold Spring Harbor, N.Y.). One library was made from poly A+ mRNA isolated form the body wall of 10-day embryos and the other from mRNA isolated from AEV-transformed chicken erythroblasts. Four distinct c-ski cDNAs were isolated; three were from the body wall library (these cloned were designated FB27, FB28 and FB29) and one cDNA clone from the erythroblast library (designated CEL). These cDNAs included sequences extending both 5' and 3' of the portion of ski present in the virus. The cDNAs demonstrate that v-ski derives from a single cellular gene and suggest that multiple c-ski mRNAs, encoding distinct ski proteins, are produced from the c-ski locus by alternate splicing (Leff et al., 1986, Ann. Rev. Biochem. 55, 1091–1117), adding to a growing list of oncogenes known to produce multiple mRNAs in this fashion (Ben-Neriah et al., 1986, Cell 44, 577–586; Levy et al., 1987, Mol. Cell. Biol. 7, 4142–4145; Martinez et al., 1987, Science 237, 411–415; McGrath et al., 1983, Nature 304, 501–506).

Structure of the cDNA Clones

The structure of all of the c-ski cDNA clones that have been characterized by DNA sequencing (Sanger et al., 1977, Proc. Natl. Acad. Sci. USA 74, 5463–5467) and their relationships to v-ski are presented in FIG. 1.

Only FB28 and CEL have sequences 5' of the v-ski sequences; both FB27 and FB29 are truncated at the 5' end. Assuming that the missing sequences at the 5' end of FB29 are similar to those in FB28 and CEL, a composite nucleotide sequence and the deduced amino acid sequence for a cDNA of the FB29 type is shown in FIG. 2. The first ATG with a substantial downstream open reading frame is located at nucleotide position 168. Upstream of this ATG no reading frames are open, suggesting that these sequences represent the 5' untranslated region.

Based on the cDNA sequence analysis and comparisons with the positions of the splice donor and acceptor sites known from the genomic sequence (Stavnezer et al., 1989, Mol. Cell. Biol. 9, 4038–4045), exon boundaries have been derived (see FIG. 3). As seen in the figure, c-ski sequences are distributed over seven exons. FB29 contains all seven exons; FB28 and FB27 lack exon 2 and exon 6, respectively. This differential splicing affects the protein coding potential of the three cDNAs.

Differential splicing of exon 2 deletes 37 amino acids without affecting the coding potential of the open reading frame downstream. Differential splicing of exon 6, however, affects the coding potential of exon 7. If exon 5 is spliced to exon 7 (seen in FB27 cDNA), a translation termination codon is generated at the splice junction and exon 7 becomes a noncoding exon. However, if exon 5 is spliced to exon 6 and exon 6 to exon 7, as in FB28/29, then the open reading frame continues in exon 7 for 417 nucleotides encoding an additional 129 amino acids.

Assuming that the missing 5' ends of the FB29 and FB27 mRNAs contain sequences identical to those present in CEL and FB28, then translation of mRNAs corresponding to the three different types of cDNAs would lead to the generation of three proteins, one containing 750 amino acids (from FB29), the second 713 amino acids (from FB28), and a third protein containing 510 amino acids (from FB27).

The CEL clone is missing 3' sequences. cDNAs that derive from the body wall (FB) library have long 3' untranslated regions that contain a 95-base pair (bp) AT-rich region from nucleotide 2803 to 2898. Within this region there are two copies of a sequence ATTA that has been implicated in mRNA destabilization in a variety of transiently induced mRNAs including c-myc, interferon, c-jun, and c-fos (Meijlink et al., 1985, Proc. Natl. Acad. Sci. USA 82, 4987–4991; Ryder et al., 1985, Proc. Natl. Acad. Sci. USA 85, 1487–1491; Shaw et al., 1986, Cell 46, 659–667). Addition or deletion of these sequences have also been shown to affect the transformation potential of c-fos (Meijlink et al., 1985, Proc. Natl. Acad. Sci. USA 82, 4987–4991).

The c-ski cDNAs contain two potential poly(A) signals (AATAAA) located at positions 3348 and 4167. Although all three clones isolated from the FB library end at the same position, none has a poly(A) tail; therefore, it is likely that the 3' ends of the c-ski mRNAs are not contained in these clones. The 4.2-kb cDNAs that were isolated and characterized are smaller than the 5.7–8.0 and 10.0-kb mRNAs detected by Northern transfer analysis (Li et al., 1986, J. Virol. 57, 1065–1072). This discrepancy has not been explained, however, it is suggested that the clones isolated so far, which lack poly(A) tails, also lack sequences from the 3' ends of the mRNAs.

The 5' End of c-ski mRNA(s)

Sequence comparisons at the 5' end reveals that both FB28 and CEL are colinear up to a position 89 bp upstream of the putative translational initiation ATG codon. FB28 has an additional 76-bp while CEL has 25 bp that are different from those found in FB28. This region where the two sequences diverge has been compared with sequences from genomic clones (Stavnezer et al., 1989, Mol. Cell. Biol. 9, 4038–4045) and the upstream sequences in the FB28 are colinear with the genomic sequences.

Examination of the sequences in the genomic DNA at the point of divergence of CEL and FB28 does not reveal consensus sequences for donor or acceptor splice sites. In order to confirm the authenticity of the clones, S1 nuclease protection analysis was carried out. The results demonstrated that the sequences present in FB28 are expressed as mRNA in normal embryos. Similar S1 analyses have provided no evidence for the presence in mRNA of the 25 bp at the extreme 5' end of the CEL clone. It is suggested that the first 25 bases of the CEL clone are the result of a cloning artefact, and that the sequences found in the FB28 clone are expressed in c-ski mRNA(s).

In an attempt to determine how much of the 5' untranslated region of the c-ski mRNA(s) are contained in FB28, primer extension analysis was carried out. Copying the 5' segment present in FB28 should give an extension product of about 280 bases. However, a primer extension product of 220 bases was seen. S1 analyses data have shown that this segment is expressed in RNA. It is possible that the observed primer extension product is the result of premature termination; however, it is also possible that there are multiple 5' ends for the c-ski mRNAs.

Organization of the Internal Exons

Sequence comparisons in the central portion of FB27, FB28 and FB29 and CEL cDNAs reveal that FB28 lacks a small region of 111 bp (exon 2) from 1079–1191 that would eliminate 37 amino acids. The genomic sequence (Stavnezer et al., 1989, Mol. Cell. Biol. 9, 4038–4045) in the corresponding region reveals the existence of consensus splice donor and acceptor sequences at the boundaries of the deletion suggesting that the cDNA derives from a differentially spliced mRNA.

In order to confirm the existence of mRNAs of the FB28 and of the FB27/29 type, S1 analysis was carried out on total RNA. Total RNA was isolated from 8, 10, 12, 15 and 17-day-old chicken embryos using standard protocols (Chirgwin et al., 1979, Biochemistry 18, 5294–5299). Approximately 20 to 30 µg of total RNA was used for nuclear S1 analysis using standard procedures (Maniatis et al., 1982, Molecular Cloning. A Laboratory Manual. Cold Spring Harbor Laboratory, Cold Spring Harbor, N.Y.).

Figure 4:
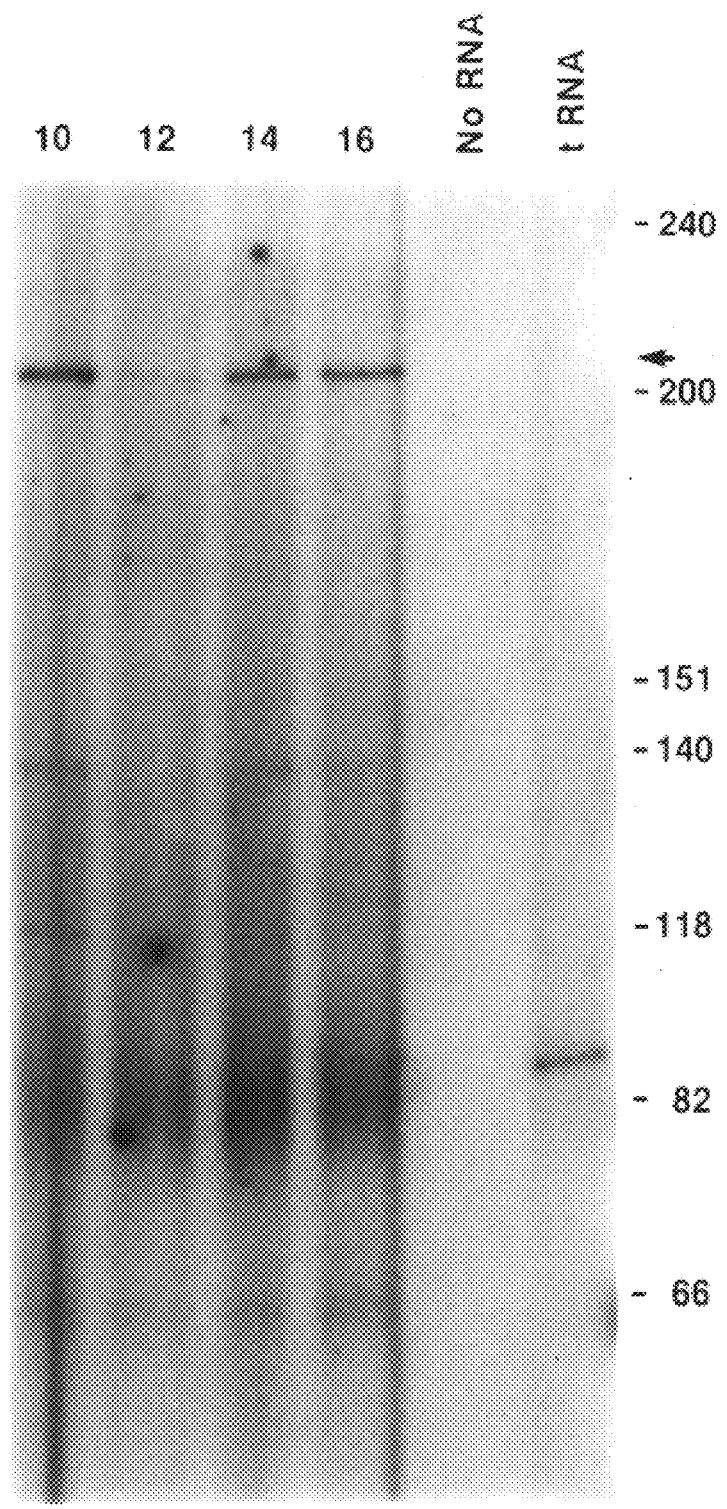
FIG. 4 and (A–D). S1 nuclease protection analysis of total RNA. Uniformly labeled single-strand probes used for hybridization are shown schematically below each picture, the thick lines represent the cDNA sequence while the thin lines represent M13 sequence. The overall length of probes and expected lengths of protected fragments are also shown. The RNA hybridization is indicated at the top of each lane. The numbers (8, 10, 12, 15 or 17) above the lane indicates the age of the embryo from which the RNA was prepared.

A uniformly labeled single-stranded probe spanning the region between the KpnI and HindIII sites of FB29/27 or FB28 (probes A and B of FIG. 1) was hybridized with total cellular RNA. As shown in FIG. 4A, hybridization to mRNA and subsequent S1 digestion of a probe derived from FB29 produced protected fragments of 645 bp indicating hybridization to mRNA of the FB27/29 type and the 262/272 bp fragments expected if the probe hybridized with mRNA of FB28 type. FB28 (probe B) protected a fragment of 534 bp (see FIG. 4B). Smaller fragments from the hybridization of the FB28 probe to mRNAs of the FB27/29 type were not observed; however, S1 does not always cleave a DNA probe efficiently opposite a looped out region of RNA. These experiments indicate that mRNA corresponding to both the FB27/29 type, containing the second exon, and FB28 type, missing the second exon, are expressed in normal cells.

Organization of the 3' Coding Exons

Sequence comparison of the three fibroblast clones demonstrated that FB28 and FB29 contain a segment (exon 6) that is absent in FB27. Examination of the genomic DNA at a position corresponding to the position where the cDNAs diverge reveals a consensus splice donor (Stavnezer et al., 1989, Mol. Cell. Biol. 9, 4038–4045). The two cDNAs appear to derive from splicing events that either include or exclude exon 6. Downstream of this alternate exon the 3' portion of all three cDNAs are identical.

To investigate whether both types of cDNAs represent normal cellular mRNA, S1 analysis was carried out. Uniformly labeled single-stranded probes were generated from an 799-bp HindIII fragment (see probe D, FIG. 1) from the 3' end of FB28 and a 497-bp HindIII fragment from the 3' end of FB27 (probe C) subcloned in M13mp18. Single-stranded probes were prepared and were hybridized to 20 $\mu$g of total RNA prepared from whole chicken embryos of different ages. As seen in FIG. 4D, hybridization of the RNA to probe D (FB28) followed by Si treatment produced a 799-bp fragment that would be expected if mRNA of FB28/29 type was present. Smaller fragments that would be generated by the FB28 probe hybridizing with mRNA of the FB27 type were not detected. S1 digestion of the FB27 probe (probe C) produced a fragment of 497-bp and also two smaller fragments of 243 to 254 bp (see FIG. 4C). It is likely that these smaller fragments derive from S1 cleavage of the FB27 probe at the site where the probe differs from mRNAs of the FB28/29 type. These data confirm the existence of the FB28/29 mRNA, but suggest that, if FB27 mRNA exists, it is likely to be present at a lower level than FB28/29.

Differential Splicing

Figure 3:
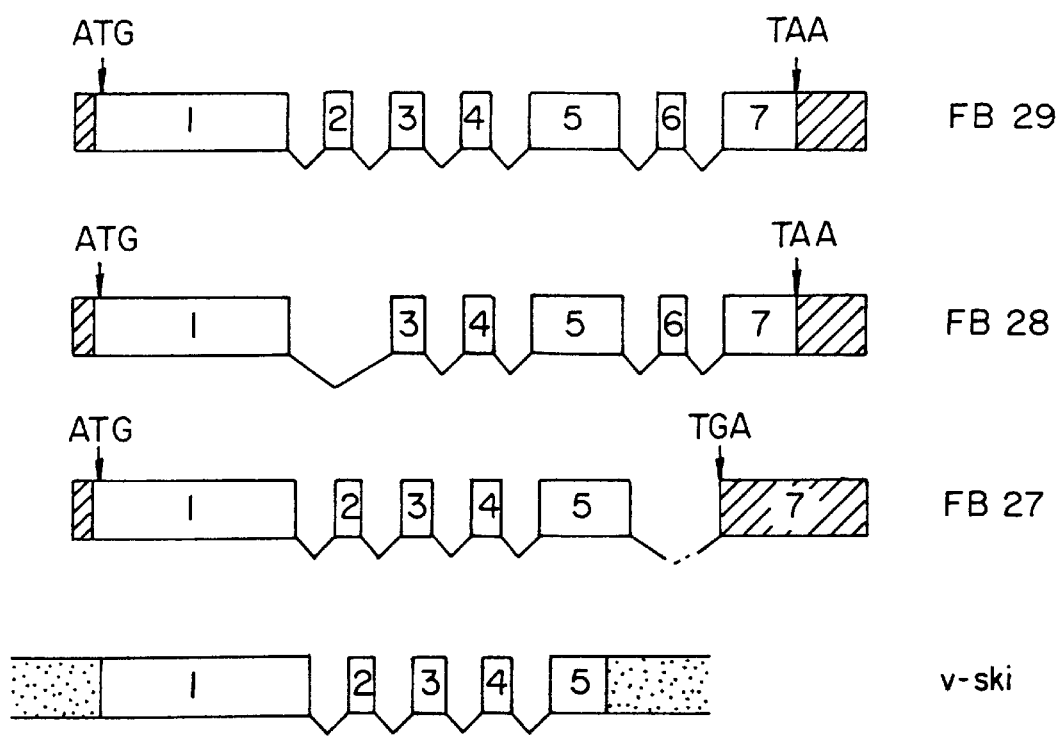
FIG. 3. Diagrammatic illustration of the alternate mRNAs generated for c-ski locus as deduced from the cDNA sequence analysis. The exons are not drawn to scale. The c-ski mRNAs are shown in relation to v-ski. The dark areas are noncoding regions while the open boxes are the protein coding regions of the cDNA. The dotted boxes on both ends of v-ski are the gag regions of the gag-ski fusion in transforming ski viruses. The relative positions of the putative translational initiation codon and the translation termination codons are also shown.

A schematic illustration of the differential splicing of three c-ski mRNAs as deduced from the nucleic acid sequence analysis of the cDNA clones is shown in FIG. 3. S1 analysis of total RNA derived from chicken embryos has confirmed the existence of two classes of mRNAs, those that do, and those that do not, contain exon 2. Using a similar protocol, the existence of mRNA that contains exon 6 was confirmed. Utilizing this technique, the existence of mRNA lacking exon 6 which would correspond to FB27 cDNA, could not be demonstrated; however, several lines of argument suggest that the FB27 cDNA is not a simple cloning artefact. The sequences absent from FB27 are bounded by apparent splice junctions (as judged by an examination of both the cDNA sequences and the available genomic DNA sequence). Although cDNAs are occasionally obtained that contain one or more introns, presumably because a partially processed mRNA was reverse transcribed, isolating cDNA artefactually missing an exon is less likely on theoretical grounds, and seems to occur rarely, if at all, in the manufacture of a cDNA library. For these reasons, the interpretation that FB27 represents a real, if relatively rare, c-ski mRNA is currently favored.

Comparison of c-ski with v-ski

Transduction of c-oncs by retroviruses often results in truncation, deletion, or point mutation(s) in the c-onc (Bishop, J. M., 1983, Ann Rev. Biochem. 52, 301–354). Comparing c-ski and v-ski sequences shows that the v-ski gene is truncated at both 5' and 3' ends and represents only part of the c-ski coding region (see FIG. 1 and 3). v-ski sequences begin at position 242 (the putative initiator ATG is at position 168) and end at position 1541 (see FIG. 3). The biological significance of the 5' and 3' truncations are unknown. There is only one base change in the v-ski relative to the c-ski, at position 1284 where v-ski has a 'C' and c-ski has a 'T'. This base change alters the amino acid from Trp in c-ski to Arg in v-ski. Deletion analysis of v-ski implies that this amino acid change does not play a significant role in the transforming potential of v-ski. The biological activities of the cDNAs are being evaluated by expressing the coding regions from the cDNAs using replication-competent retroviral vectors (Hughes et al., 1987, J. Virol. 61, 3004–3012).

As shown in FIG. 5, 18 of 20 bp are identical between c-ski and the p19 region of gag in the parental ALV. This region of homology contains the 5' junction between viral sequences and v-ski. With such a long stretch of homology, it is impossible to assign the 5' recombinational joint precisely. No substantial homology can be seen precisely at the 3' ski/ALV joint. However, just downstream of the 3' junction, there is an ALV sequence that is closely homologous to a segment of c-ski found just 3' of the v-ski/AVL junction. It is possible to invoke this region of homology in the alignment of the nucleic acids involved in the recombination event.

Transduction Mechanism

The exact mechanism(s) by which retroviruses acquire cellular oncogenes remains uncertain. It has been suggested that as a first step, the viral DNA is integrated next to or within a cellular oncogene (Bishop, J. M., 1983, Ann Rev. Biochem. 52, 301–354). The retroviral and cellular sequences can then be fused by DNA deletion events (Bishop, J. M. 1983, Ann. Rev. Biochem. 52, 301–354; Czernilofsky et al., 1983, Nature 301, 736–738) or RNA read through (Herman et al., 1987, Science 236, 845–848; Nilsen et al., 1985, Cell 41, 1719–726); however, homology is not known to be involved in either of these processes. In the case of ski, a comparison of c-ski sequences with the p19 coding region implies that some event in the generation of the ski viruses involved homologous recombination. However, the homologous recombination event may be secondary. If the original event were nonhomologous and generated a viral genome that contained a direct repeat, it would be expected, as has been observed for Rous sarcoma virus, that sequences between the repeats could be lost by recombination during viral passage, presumably through copy choice during reverse transcription. It is possible, however, to propose models in which the oncogene is acquired by homologous recombination between the c-onc and the replication competent viruses. Short stretches of homologies have been observed at both ends of viral oncogenes (Banner et al., 1985, Mol. Cell. Biol. 5, 1400–1407; Van Beveren et al., 1983 Cell 32, 1241–1255) or only at the left hand or 5' recombination joint (Besmer et al., 1986, Nature (London) 320, 415–421; Roebroek et al., 1987, J. Virol. 61, 2009–2016). The present data does not allow the determination of whether the 5' homologous recombination event was primary or secondary.

Transgene and Generation of the Transgenic Mice

The largest form of the isolated cDNAs, that is FB29 which contains sequences that derive from all seven coding exons of c-ski, and judged by DNA sequence, encodes a c-ski protein of 750 amino acids, was used to create the derivative ΔFB29. ΔFB29 has a frameshift mutation at position 1475 in the fifth coding exon (one C in a run of five Cs was lost in the frameshift mutant), and is predicted to give rise to a protein of 448 amino acids of which the first 436 are identical to the first 436 amino acids of the FB29 form of c-ski (the last 12 amino acids are past the frameshift mutation and thus differ from those of the FB29 form of c-ski). ΔFB29 used in the generation of a the transgene is shown schematically in FIG. 6.

The construction of the ski portion of the transgene is already described (Sutrave and Hughes, 1989, Mol. Cell. Biol. 9, 4046–4051; Sutrave et al., 1990, Mol. Cell. Biol. 10, 3137–3144). Briefly, a truncated chicken c-ski cDNA called ΔFB29 had been previously cloned into the adaptor plasmid Cla12Nco. The ΔFB29 segment was released from the adaptor plasmid by Cla1 digestion and the 5' overhangs filled in using the Klenow fragment of E. coli DNA polymerase I and all four dNTPs. This blunt-ended fragment was ligated to the pMEX neo vector which have been digested with EcoR1 restriction enzyme and blunt-ended with the Klenow fragment. Clones were selected that had inserts in the correct orientation and were digested with both PvuI and Nru1 restriction endonucleases. These enzymes release a segment that contains the ΔFB29 cDNA flanked by an MSV LTR and the SV40 polyA signal (see FIG. 6). This fragment was gel purified and used to inject fertilized mouse eggs [Hogan et al., 1986, Manipulating the mouse embryo. A Laboratory Manual. (Cold Spring Harbor, N.Y.: Cold Spring Harbor Laboratory)].

The ΔFB29 clone was placed in the pMEX expression plasmid in such an orientation that the truncated c-ski cDNA between an MSV LTR and an SV40 polyadenylation site (see FIG. 6). The plasmid (named MSV-SKI has been deposited at the American Type Culture Collection, Rockville, Md. and has been given ATCC accession number 68044) was digested with PvuI and NruI to release the expression cassette. The expression cassette was purified by gel electrophoresis and introduced into fertilized mouse eggs by microinjection. Forty-four founder mice were obtained after two independent injections. The mice were identified by dot blot analysis of DNA isolated from tail clips. This analysis was confirmed by Southern transfer. Three of the 44 founder mice showed a distinct muscle phenotype (TG 8566, TG 8821, and TG 8562). These three founders and a single mouse that contained unrearranged copy of the complete transgene but did not show any phenotype (TG 8542) were used to generate lines. Southern transfer analysis of DNA from TG 8566, TG 8821, TG 8562, and TG 8542 suggests that the site of integration of the transgene in each line is different and the copy number varies from approximately 5–35 copies per genome.

DNA positive mice from the three lines (TG 8566, TG 8821 and TG 8562) had a similar distinct appearance resulting from abnormal muscle growth. Although the three lines of mice carry an oncogene, none of the lines appears to have an increased incidence of tumors. This result is not totally unexpected, since the v-ski virus is not tumorigenic in chickens unless the birds are injected with infected cells (E. Stavnezer, 1988, in The Oncogene Handbook, E. P. Reddy, A. Skalka, and T. Curran, eds. (Amsterdam: Elsevier Science Publishing Co.), pp. 393–401). The three strains of mice do not express high levels of the transgene except in skeletal muscle. This is consistent with the interpretation that c-ski affects skeletal muscle cells directly and not as a secondary consequence of altered motor neuron function.

The majority of the skeletal muscles are involved. Mice with this phenotype can be readily identified by looking for enlarged limb and jaw muscles (FIG. 7). Since the phenotype was obtained with three separate founders, the most reasonable explanation is that the phenotype was caused by the chicken c-ski transgene. Therefore, all four lines of mice were examined, the three with the muscular phenotype and the one line that did not have an observable phenotype, for the expression of the transgene.

Full length c-ski cDNAs FB27 and FB29 were cloned into the pMEX expression plasmid, as previously described for ΔFB29, in such a manner that the c-ski cDNA was between the MSV LTR and an SV40 polyadenylation site in the proper orientation. The plasmids were designated pMNSK27 and pMNSK29. The plasmids were each separately digested with PvuI and NruI to release the expression cassette. The two expression cassettes were each purified by gel electrophoresis and independently introduced into fertilized mouse eggs by microinjection [Hogan et al., 1986, Manipulating the mouse embryo. A laboratory embryo. A Laboratory Manual. (Cold Spring Harbor, N.Y.: Cold Spring Harbor Laboratory)]. Twenty-one founder mice containing FB27 and fourteen founder mice containing FB29 were obtained after independent injections. The mice were identified by dot blot analysis of DNA isolated from tail clips. Three of the FB27-containing founder mice and one of the FB29-containing founder mice showed a distinct muscle phenotype. Mice with this phenotype were readily identified by looking for enlarged limb and jaw muscles. These founders were used to generate lines (lines 21499, 21508, and 21540 contained FB27 and line 21428 contained FB29).

Generation of Transgenic Pigs

The c-ski expression cassette (FIG. 6, containing ΔFB29) was introduced into pigs. The plasmid DNA (named MSV-SKI, ATCC accession number 68044) was digested with PvuI and NruI and the expression cassette (FIG. 6) was purified as described for mice. Microinjection of pig ova was similar to that described for mice except for the modification that pig ova were centrifuged as described by Wall (1985) Biol. of Reproduction 32:645–651 prior to microinjection (Hammer et al. (1985) Nature 315:680–683). Twenty-nine pigs containing ΔFB29 were obtained after injection (Table 1). The pigs were identified by dot blot analysis of DNA isolated from tail clips (Siracusa et al. (1987) Genetics 117:85–92). Three of the transgenic pigs had distinct muscle hypertrophy (FIG. 15). Two pigs (3-0202 and 3-0503) had hypertrophy of hip and thigh muscles of rear quarters and hypertrophy of shoulder muscles of the fore quarters. Pig number 3-0102 had evidence of hypertrophy of shoulder muscles of the fore quarters.

TABLE 1

List of transgenic pigs

| Pig No. | Sex | Born | Observation |
|---------|-----|------|-------------|
| 2-9405 | F | 5/17/90 | |
| 2-9407 | M | 5/17/90 | |
| 2-9503 | F | 5/17/90 | Myopathy |
| 2-9902 | M | 5/31/90 | |
| 3-0102 | F | 5/31/90 | Muscle Hyp. |
| 3-0202 | F | 5/31/90 | Muscle Hyp. |
| 3-0208 | M | 5/31/90 | |
| 3-0501 | F | 6/4/90 | Myopathy |
| 3-0503 | M | 6/4/90 | Muscle Hyp. |
| 3-1102 | M | 6/14/90 | |
| 3-1105 | F | 6/14/90 | Myopathy |
| 3-1107 | M | 6/14/90 | Myopathy |

TABLE 1-continued

List of transgenic pigs

| Pig No. | Sex | Born | Observation |
|---|---|---|---|
| 3-1108 | M | 6/14/90 | |
| 3-1110 | F | 6/14/90 | Stillborn |
| 3-1504 | F | 6/21/90 | |
| 3-1603 | F | 6/21/90 | Myopathy |
| 3-1705 | M | 6/21/90 | |
| 3-1708 | F | 6/21/90 | |
| 3-1709 | M | 6/21/90 | |
| 3-2511 | F | 7/5/90 | Stillborn |
| 3-2808 | F | 7/26/90 | |
| 3-3010 | M | 8/2/90 | |
| 3-3304 | F | 8/10/90 | |
| 3-3703 | F | 8/16/90 | |
| 3-3801 | M | 9/6/90 | |
| 3-3808 | M | 9/6/90 | |
| 3-3908 | F | 9/6/90 | |
| 3-4004 | M | 9/21/90 | |
| 3-4106 | M | 9/21/90 | |

DNA/RNA Analysis

Total cellular DNA and RNA were isolated by standard procedures. For RNA isolation, tissues were frozen in liquid nitrogen immediately following dissection and homogenized in RNAzol (Cinna Biotex) and processed according to the manufacturer's recommendation. For Northern transfer analysis, approximately 20 μg of total RNA from different tissues was fractioned by electrophoresis on 1.5% agarose gels containing 2.2 M formaldehyde. The RNA was transferred to nitrocellulose membranes and probed either with a nick-translated chicken ski cDNA or a chicken β-actin cDNA. The coding region of the β-actin cDNA cross reacts with the messages for the other actions and can be used to validate the quantity and quality of RNA from most tissues.

Total RNA from spleen, lung, brain, kidney, liver, stomach, heart, and leg (skeletal) muscle of transgenic mice was isolated as described and the results are shown in FIG. 8. All three lines with the phenotype (TG 8566, TG 8821 and TG 8562) expressed a 2.5-kb chicken c-ski specific transcript at high levels in skeletal muscle; however, some lines of mice showed low levels of chicken c-ski RNA in other tissues. The TG 8562 line has RNA from the transgene in the heart, although at a lower level than in skeletal muscle. Histopathology of hearts from TG 8562 mice showed that there is no significant effect on this tissue. Line TG 8542, which does not show any phenotype, had a much lower level of RNA from the transgene in muscle than did the lines that showed the phenotype. The observation that expression was restricted to muscle was unexpected since the MSV LTR has been shown to express in a variety of tissues when linked to other genes (Khillan et al., 1987, Genes Dev. 1, 1327–1335).

To determine whether the transcript was initiated at the proper site in tissues expressing the ski transgene, RNase protection assays were carried out as described by Melton (Melton et al., 1984, Nucl. Acids Res. 12, 7035–7036). A 1.8-kb Pvu1 to Bgl1 fragment was subcloned in Bluescript KS vector and used to generate radioactively labeled RNA from the T7 promoter. Approximately 10 μg of total RNA was hybridized with 5×10⁵ cpm of probe. The hybridizations were carried out overnight at 50° C. in 80% formamide and 1× buffer (5× hybridization buffer is 0.2 M Pipes, pH 6.4, 2 M sodium chloride, 5 mM EDTA). After hybridization, the samples were diluted in ribonuclease digestion buffer (10 mM Tris Cl, pH 7.5, 0.3 M sodium chloride, 5 mM EDTA) and treated with RNase T1 at a concentration of 1 u/μl for 60 min at 30° C. The RNase digestions were stopped by adding 10 μl of 20% SDS and 4 μl of Proteinase K (stock 10 mg/ml) and incubating at 37° C. for 15 min. The digested samples were extracted with phenol chloroform (1:1 mixture) and ethanol precipitated with carrier tRNA. The pellet was rinsed once with 70% ethanol, dried and dissolved in formamide containing bromophenol blue and xylene cyanol dyes. The samples were denatured at 100° C. and separated on 6% polyacrylamide gels containing 7.5 M urea.

Uniformly labeled antisense RNA was generated by T7 RNA polymerase from a fragment that spans the MSV LTR and c-ski (see FIG. 9). Using RNA from the three positive transgenic lines of mice, a protected fragment of approximately 980 bases was seen, which is the expected size if the transcript is initiated at the authentic initiation site within the MSV LTR (FIG. 9). This analysis also gives a more quantitative estimate of the level of transgene RNA in the heart and skeletal muscle of both the phenotypically positive and the phenotypically negative lines of mice. FIG. 9 shows that the level of transgene RNA in the heart of TG 8821 is much lower (estimated at perhaps 1/10–1/20) than the level found in the skeletal muscle. In addition, this analysis shows that the phenotypically negative line, TG 8542, has a low but detectable level of transgene RNA in skeletal muscle. These data suggest not only that the muscular phenotype is associated with the expression of the chicken c-ski transgene, but also that a minimum threshold level of c-ski RNA must be reached to produce the muscular phenotype. In fact, these data suggest that the minimal threshold level to see an effect of the transgene is high, probably several thousand-fold the levels of endogenous c-ski expression in the chicken tissues examined (Sutrave and Hughes, 1989, Mol. Cell. Biol. 9, 4046–4051).

Protein Analysis

The underlying assumption is not that the expression of the c-ski RNA gives rise directly to the muscular phenotype, but rather that the phenotype results from the presence of the c-ski protein. Accordingly, the c-ski protein was looked at in Western transfer assays. Although rabbit antisera have been prepared that specifically recognize the 50-kd form of c-ski (Sutrave et al., 1990, Mol. Cell. Biol. 10, 3137–3144), these antisera do not work well in Western transfer assays. Mouse monoclonal antibodies that recognize c-ski and that work well in Western transfer assays have been developed, however, the use of these reagents presents a technical problem. These monoclonals were not available in sufficient quantity to permit direct labeling. Indirect labeling procedures using, for example, labeled rabbit anti mouse detect not only the anti ski monoclonal but also the endogenous mouse heavy chain, which comigrates with the 50-kd form of c-ski made from the transgene. To avoid this problem, extracts of muscle and control tissue (liver) from normal controls and from the transgenic mice were prepared. The endogenous mouse antibodies were removed from these extracts by precipitation with rabbit anti mouse antibody as described below.

For detection of ski protein in tissues from the transgenic and control mice, 1–5 mg of tissue was homogenized in 1 ml of RIPA buffer, 20 mM Tris Cl pH 7.5, 150 mM NaCl, 0.5% SDS, 0.5% NP40, 0.5% sodium deoxycholate, 1 mM EDTA, 1 mM PMSF, and 35 μ/ml of aproteinin. The homogenate was clarified by centrifugation at 10,000 rpm for 10 min. Mouse IgG was removed from 100 μl of the supernatant by incubation with 10 μl of 1 mg/ml rabbit anti mouse IgG (in PBS) for 2 hr on ice. The complex was removed by adding 100 μl of 40% protein A sepharose beads in RIPA buffer. The resulting supernatant was collected and 20 μl was fractionated on 10% SDS polyacrylamide gels. The proteins were transferred to nitrocellulose membranes overnight in buffer containing 0.125 M Tris Cl, 0.092 M Glycine and 20% Methanol, pH 8.3. The filters were blocked with 4% dry nonfat milk in TBS buffer (0.5 M Tris Cl, pH 7.4 and 0.2 M sodium chloride) for 2 hr at room temperature and incubated with a mixture of three anti-ski monoclonal antibodies at a dilution of 1:3000 for 2 hr at room temperature and were then washed 3× with TBS. Secondary incubations with rabbit anti mouse IgG were done for 2 hr at room temperature (1:2000 dilution from a 1 mg/ml stock). The filter was washed as described above and finally incubated with 5 $\mu$Ci of $^{125}$I protein A (Amersham, sp. act. 30 mCi/mg) for 2 hr at room temperature. The filter was washed 3× with TBS and exposed to XAR Kodak film at −70° C. for 6 days.

Only affected tissues (skeletal muscle) from the transgenic animals contain the 50-kd c-ski protein (FIG. 10). These data also suggest that there may be differences in the level of the c-ski protein in the muscles of the three positive lines; however, the complexities of the manipulations in this experiment make quantitative interpretation a questionable proposition.

Histology

For histology, selected muscles from the line TG 8566 were isolated so that they remained attached at their origin and insertion and they were then fixed in 2% formaldehyde, 2% gluteraldehyde. Fixed muscle were transected precisely through the middle of the muscle belly and embedded in JB4 plastic (Polysciences, PA).

For immunocytochemistry, tissues were snap frozen in isopentane cooled in liquid nitrogen. The procedure for immunochemical staining was as outlined in Narusawa et al. [(1987), J. Cell. Biol. 104, 447–459].

The results showed that not only is expression of the transgene and its effect restricted to muscle, the expression and the effects appear, at least in the line TG 8566, to be confined to certain muscles, and apparently to specific fiber types. However, the affected fibers are not all of the same type.

The myocardium was normal and there were no abnormalities of visceral smooth muscle in these animals. FIGS. 11a and 11b compare cross sections made precisely through the middle of the plantaris muscle from mature male controls and transgenic mice. Cross sectional area of the control is 2.7$\mu^2$ and that of the TG 8566 mouse is 9.4$\mu^2$, more than twice the control value. This massive growth is generalized. Comparable increases in cross section were found in almost all axial and appendicular muscles throughout male and female mice of line TG 8566. Only three muscles were found that appear to be normal: the tongue, the diaphragm, and the soleus; these are the same size in transgenic as in control muscles (see FIG. 12). RNA was isolated from the diaphragm and soleus muscles of TG 8566 mice. Northern transfer analysis shows that the level of chicken c-ski RNA is much lower in these two phenotypically normal muscles than in the affected muscles from the same line (FIG. 13).

The most obvious additional gross morphologic abnormality is that transgenic animals were almost totally devoid of fat whereas control animals contained substantial amounts of subcutaneous and intraperitoneal fat. For this reason, there is little difference in weights between control and TG 8566 mice. There are also skeletal abnormalities; the tibia of transgenic animals is normal in size but was bowed cranially, apparently as an adaptation to accommodate the more than two-fold increase in size of the anterior tibia and extensor digitorum muscles.

The muscles in control mice are made up of fibers with a range of cross sectional areas. The range of sizes is greatly extended in TG 8566 mice (FIGS. 11 and 12). Not all fibers are affected; the hypertrophy is limited to a select population of fibers (FIG. 11d). Hypertrophy of these fibers apparently accounts for the increase in muscle mass in line TG 8566. No evidence was found that the numbers of fibers is significantly increased in individual muscles. For example, the population of fibers in the control plantaris is 912±111 (n=3) and in TG 8566 is 991±87 (n=3). Similarly, no difference in the total number of fibers in the extensor digitorum longus muscle of TG 8566 and control mice was found.

Figure 14A:
Figure 14B:
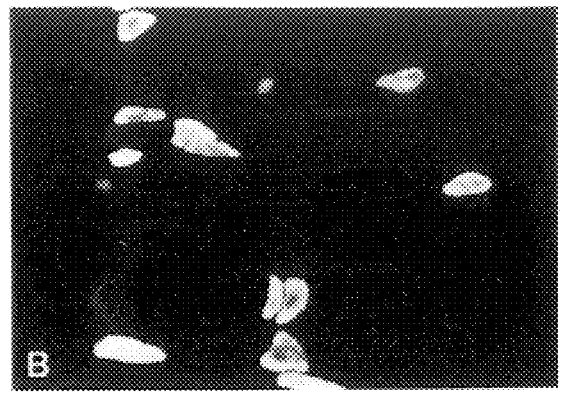
Figure 14C:
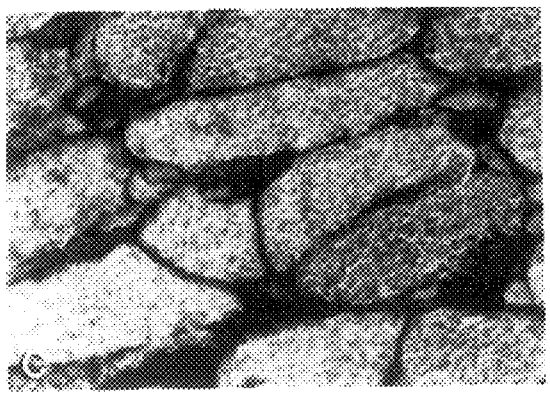

To investigate which types of fibers are affected in the line TG 8566, three monoclonal antibodies were used that specifically recognize slow myosin heavy chains (MHC) (NOQ7 5 4D, Narusawa et al., 1987, J. Cell Biol. 104, 447–459), all fast MHCs (2G3, Narusawa et al., 1987, J. Cell Biol. 104, 447–459) type II a fast MHC (SC 7 11, Schiaffino et al., 1989, J. Muscle Res. and Cell Motil. 10, 197–205) and type IIb fast MHC (BF-F3, Schiaffino et al., 1989, J. Muscle Res. and Cell Motil. 10, 197–205). FIG. 14 shows immunofluorescent staining of sections from the rhomboideus capitis muscle with these three antibodies. No evidence was found that slow fibers are enlarged (FIG. 14a) and the total number of slow fibers in the rhomboideus capitis from a TG 8566 mouse (120) approximates the number found in rhomboideus capitis from control mice (117). Type IIa fibers are also not affected (FIG. 14b). Many of the type IIa fibers lie between hypertrophied fibers and are frequently distorted in shape as if compressed by the expansion of their neighbors (FIG. 14b).

Figure 14D:
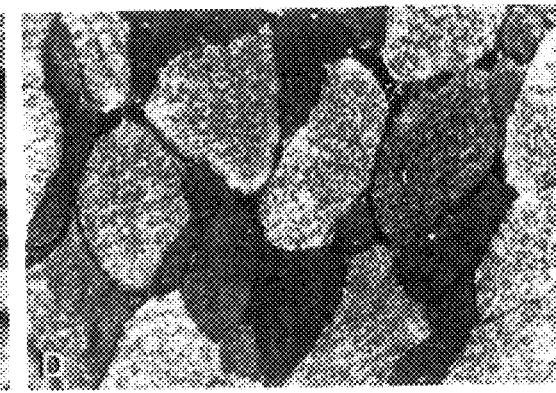

The small, fast IIa fibers and all of the hypertrophied fibers stain with the monoclonal antibody 2G3 (FIG. 14c) indicating that all hypertrophied fibers are fast. In the rhomboideus capitis, most, but not all, large fibers also stain with the monoclonal antibody BF-F3 that is specific for IIb MHC (FIG. 14d). In the plantaris, there is more variation in reactivity and only 50% of hypertrophied fibers stain with BF-F3. These results show that the hypertrophic modification of fibers in TG 8566 mice involves at least two types of fast fibers. One of these is type IIb. By exclusion, we suggest that the others are IIx fibers (Schiaffino et al., 1989, J. Muscle Res. and Cell Motil. 10, 197–205; Termin et al., 1989, Histochemistry 92, 453–457; Gorza, 1990, J. Histochem. Cytochem. 38, 257–265).

Variation in staining of hypertrophic fibers with the actomyosin ATPase histochemical reaction after acid preincubation, DPNH staining for mitochondrial enzyme activity and PAS staining all support the conclusion that more than one fast fiber type is affected in this line of transgenic mice. These results also support the interpretation that both IIb and IIx fibers are hypertrophied.

Occasional necrotic and regenerating fibers were found in some, but not all, muscles of line TG 8566 mice. In the hind limb, these appeared to be most prevalent in the anterior tibial muscle; they were never found in the rhomboideus capitis, a superficial muscle of the neck.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A non-human transgenic mammal whose genome comprises a DNA construct comprising a DNA segment encoding a c-ski protein operably linked to a promoter heterologous to the endogenous c-ski gene effective for expression in muscle cells, wherein expression of said DNA construct in muscle cells results in an increase in muscle mass of said mammal.

2. The non-human mammal according to claim 1 wherein said DNA construct has been introduced into an ancestor of said mammal.

3. The non-human mammal according to claim 1 wherein said DNA construct is introduced to said mammal or ancestor of said mammal at an embryonic stage.

4. The non-human mammal of claim 2 wherein said c-ski protein is a chicken c-ski protein.

5. The non-human mammal according to claim 1 wherein said c-ski protein is a truncated c-ski protein.

6. The non-human mammal according to claim 5 wherein said DNA segment encoding a c-ski protein is ΔFB29.

7. The non-human mammal according to claim 1 wherein said DNA segment encoding a c-ski protein is FB29.

8. The non-human mammal according to claim 1 wherein said DNA segment encoding a c-ski protein is FB27.

9. The non-human mammal according to claim 1 wherein said DNA construct is from a pMEX expression plasmid containing said DNA segment encoding a c-ski protein.

10. The non-human mammal according to claim 1 wherein said DNA construct is a pMEX expression plasmid containing said DNA segment encoding a c-ski protein.

11. The non-human mammal according to claim 1 wherein said mammal is a mouse.

12. The non-human mammal according to claim 1 wherein said mammal is a pig.

13. The non-human mammal according to claim 1 wherein said mammal is a bovine.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 4175 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 168..2417
       (D) OTHER INFORMATION: /product= "chicken c-ski FB29 type"

(ix) FEATURE:
       (A) NAME/KEY: exon
       (B) LOCATION: 168..1079

(ix) FEATURE:
       (A) NAME/KEY: exon
       (B) LOCATION: 1080..1190

(ix) FEATURE:
       (A) NAME/KEY: exon
       (B) LOCATION: 1191..1316

(ix) FEATURE:
       (A) NAME/KEY: exon
       (B) LOCATION: 1317..1432

(ix) FEATURE:
       (A) NAME/KEY: exon
       (B) LOCATION: 1433..1698

(ix) FEATURE:
       (A) NAME/KEY: exon
       (B) LOCATION: 1699..2000

(ix) FEATURE:
       (A) NAME/KEY: exon
       (B) LOCATION: 2001..2417

(ix) FEATURE:
       (A) NAME/KEY: misc_feature
       (B) LOCATION: 243..1541
       (D) OTHER INFORMATION: /product= "v-ski"

(ix) FEATURE:
       (A) NAME/KEY: variation
       (B) LOCATION: replace(1284, "Y")
       (D) OTHER INFORMATION: /note= "position 1284 in c-ski = T;
           position 1284 in v-ski = C"

(xi) SEQUENCE DESCRIPTION: SEQ ID NO:1:

```
TCCTCGTCGT CTGTGGATTG CTAAACCTGA GTGGGAAGGG GGGGGAAAAA AAAAAGGGTG         60

GGTTGTTGTT TTGTTTAAAA AAAGAAAAAA TCCCTTAAGT GGATTTGTAC CAGCGTGGAA        120

GATAACTGGG GATTTTTGTT GTTTGTTTTG GGAATAGAAA CTAAAAA ATG GAG ACT         176
                                                 Met Glu Thr
                                                   1

GTA AGT AGA AGC AGC TTC CAG CCT CAT CCA GGA CTG CAG AAG ACC TTG         224
Val Ser Arg Ser Ser Phe Gln Pro His Pro Gly Leu Gln Lys Thr Leu
      5                  10                  15

GAA CAG TTT CAT CTG AGC TCT ATG AGC TCC CTG GGT GGC CCT GCT GCT         272
Glu Gln Phe His Leu Ser Ser Met Ser Ser Leu Gly Gly Pro Ala Ala
 20                  25                  30                  35
```

```
TTC TCA GCG CGA TGG GCA CAG GAG ATG TAC AAG AAA GAC AAT GGC AAA      320
Phe Ser Ala Arg Trp Ala Gln Glu Met Tyr Lys Lys Asp Asn Gly Lys
            40                  45                  50

GAC CCA GCG GAA CCT GTA CTG CAT CTG CCC CCT ATC CAG CCC CCC CCG      368
Asp Pro Ala Glu Pro Val Leu His Leu Pro Pro Ile Gln Pro Pro Pro
                55                  60                  65

GTG ATG CCT GGT CCC TTC TTC ATG CCC TCG GAC AGA TCC ACT GAG AGG      416
Val Met Pro Gly Pro Phe Phe Met Pro Ser Asp Arg Ser Thr Glu Arg
        70                  75                  80

TGC GAG ACC ATC CTG GAA GGG GAA ACC ATC TCC TGC TTC GTG GTG GGT      464
Cys Glu Thr Ile Leu Glu Gly Glu Thr Ile Ser Cys Phe Val Val Gly
    85                  90                  95

GGG GAA AAG CGC CTT TGC TTG CCC CAG ATC CTG AAC TCG GTG CTC AGG      512
Gly Glu Lys Arg Leu Cys Leu Pro Gln Ile Leu Asn Ser Val Leu Arg
100                 105                 110                 115

GAC TTC TCC CTG CAG CAG ATC AAT TCG GTG TGC GAT GAG CTA CAC ATT      560
Asp Phe Ser Leu Gln Gln Ile Asn Ser Val Cys Asp Glu Leu His Ile
                120                 125                 130

TAC TGC TCC AGA TGC ACC GCT GAC CAG CTG GAG ATC CTC AAA GTC ATG      608
Tyr Cys Ser Arg Cys Thr Ala Asp Gln Leu Glu Ile Leu Lys Val Met
            135                 140                 145

GGC ATC TTG CCC TTC TCT GCC CCC TCC TGC GGG CTG ATC ACT AAA ACT      656
Gly Ile Leu Pro Phe Ser Ala Pro Ser Cys Gly Leu Ile Thr Lys Thr
        150                 155                 160

GAT GCT GAG AGG CTT TGC AAT GCC TTG CTT TAT GGT GGC ACC TAT CCT      704
Asp Ala Glu Arg Leu Cys Asn Ala Leu Leu Tyr Gly Gly Thr Tyr Pro
    165                 170                 175

CCC CAC TGC AAG AAG GAA TTC TCT AGC ACG ATT GAG CTG GAG CTT ACA      752
Pro His Cys Lys Lys Glu Phe Ser Ser Thr Ile Glu Leu Glu Leu Thr
180                 185                 190                 195

GAG AAG AGC TTC AAG GTG TAC CAC GAG TGC TTT GGG AAG TGT AAG GGA      800
Glu Lys Ser Phe Lys Val Tyr His Glu Cys Phe Gly Lys Cys Lys Gly
                200                 205                 210

CTC CTG GTA CCA GAG CTT TAC AGT AAC CCC AGC GCA GCC TGC ATC CAG      848
Leu Leu Val Pro Glu Leu Tyr Ser Asn Pro Ser Ala Ala Cys Ile Gln
            215                 220                 225

TGC TTG GAC TGC AGG CTC ATG TAC CCG CCT CAC AAA TTT GTG GTC CAC      896
Cys Leu Asp Cys Arg Leu Met Tyr Pro Pro His Lys Phe Val Val His
        230                 235                 240

TCT CAC AAA TCC CTG GAA AAC AGG ACT TGC CAC TGG GGC TTT GAC TCT      944
Ser His Lys Ser Leu Glu Asn Arg Thr Cys His Trp Gly Phe Asp Ser
    245                 250                 255

GCA AAC TGG AGG TCC TAC ATC CTC CTT AGC CAG GAT TAC ACT GGG AAA      992
Ala Asn Trp Arg Ser Tyr Ile Leu Leu Ser Gln Asp Tyr Thr Gly Lys
260                 265                 270                 275

GAG GAG AAA GCT AGG CTG GGC CAG CTC TTA GAT GAA ATG AAA GAA AAA     1040
Glu Glu Lys Ala Arg Leu Gly Gln Leu Leu Asp Glu Met Lys Glu Lys
                280                 285                 290

TTT GAC TAT AAC AAC AAA TAC AAG AGG AAA GCC CCC AGG AAC CGT GAG     1088
Phe Asp Tyr Asn Asn Lys Tyr Lys Arg Lys Ala Pro Arg Asn Arg Glu
            295                 300                 305

TCT CCT AGA GTT CAG CTC CGC CGG ACC AAA ATG TTC AAG ACA ATG CTG     1136
Ser Pro Arg Val Gln Leu Arg Arg Thr Lys Met Phe Lys Thr Met Leu
        310                 315                 320

TGG GAT CCA GCT GGA GGT TCA GCG GTA CTG CAG CGT CAG CCA GAT GGA     1184
Trp Asp Pro Ala Gly Gly Ser Ala Val Leu Gln Arg Gln Pro Asp Gly
    325                 330                 335

AAT GAG GTC CCT TCA GAT CCT CCT GCT TCC AAG AAA ACC AAA ATA GAC     1232
Asn Glu Val Pro Ser Asp Pro Pro Ala Ser Lys Lys Thr Lys Ile Asp
```

```
                    -continued 340                 345                 350                 355

GAC TCC GCT TCC CAA TCT CCA GCT TCT ACT GAG AAG GAA AAG CAG TCC   1280
Asp Ser Ala Ser Gln Ser Pro Ala Ser Thr Glu Lys Glu Lys Gln Ser
                360                 365                 370

AGT YGG TTA CGG TCC TTA TCC AGT TCA TCT AAT AAG AGC ATT GGC TGT   1328
Ser Xaa Leu Arg Ser Leu Ser Ser Ser Ser Asn Lys Ser Ile Gly Cys
        375                 380                 385

GTC CAT CCC CGT CAG CGT CTC TCA GCT TTC CGG CCC TGG TCC CCT GCT   1376
Val His Pro Arg Gln Arg Leu Ser Ala Phe Arg Pro Trp Ser Pro Ala
            390                 395                 400

GTA TCA GCA AAT GAG AAA GAG CTC TCA ACC CAT CTT CCT GCA TTG ATC   1424
Val Ser Ala Asn Glu Lys Glu Leu Ser Thr His Leu Pro Ala Leu Ile
                405                 410                 415

CGA GAC AGC AGT TTT TAC TCC TAC AAA AGC TTT GAG AAT GCT GTG GCC   1472
Arg Asp Ser Ser Phe Tyr Ser Tyr Lys Ser Phe Glu Asn Ala Val Ala
420                 425                 430                 435

CCC AAC GTG GCA CTC GCA CCT CCT GCC CAA CAG AAA GTT GTG AGC AAC   1520
Pro Asn Val Ala Leu Ala Pro Pro Ala Gln Gln Lys Val Val Ser Asn
                    440                 445                 450

CCA CCC TGT GCC ACA GTG GTG TCC CGG AGC AGC GAA CCG CCG AGC AGC   1568
Pro Pro Cys Ala Thr Val Val Ser Arg Ser Ser Glu Pro Pro Ser Ser
                455                 460                 465

GCT GCG CAG CCA CGG AAA AGA AAA CAT GCT GCA GAA ACC CCG GCT GTC   1616
Ala Ala Gln Pro Arg Lys Arg Lys His Ala Ala Glu Thr Pro Ala Val
            470                 475                 480

CCA GAG CCA GTG GCC ACG GTT ACT GCC CCT GAA GAG GAT AAG GAA TCA   1664
Pro Glu Pro Val Ala Thr Val Thr Ala Pro Glu Glu Asp Lys Glu Ser
485                 490                 495

GAA GCA GAA ATT GAA GTA GAG ACC AGG GAG GAA TTC ACC TCC TCC TTA   1712
Glu Ala Glu Ile Glu Val Glu Thr Arg Glu Glu Phe Thr Ser Ser Leu
500                 505                 510                 515

TCC TCG CTC TCC TCC CCA TCC TTT ACT TCA TCC AGC TCT GCA AAG GAC   1760
Ser Ser Leu Ser Ser Pro Ser Phe Thr Ser Ser Ser Ser Ala Lys Asp
                520                 525                 530

ATG AGC TCA CCT GGG ATG CAA GCC CCA GTC CCA GTC AAC AGT TCA TAT   1808
Met Ser Ser Pro Gly Met Gln Ala Pro Val Pro Val Asn Ser Ser Tyr
            535                 540                 545

GAG GTT GCA GCA CAT TCT GAC TCT CAC AGC AGT GGG TTG GAA GCT GAG   1856
Glu Val Ala Ala His Ser Asp Ser His Ser Ser Gly Leu Glu Ala Glu
        550                 555                 560

CTG GAG CAC CTA AGG CAG GCC CTG GAC AGT GGC CTA GAT ACA AAA GAA   1904
Leu Glu His Leu Arg Gln Ala Leu Asp Ser Gly Leu Asp Thr Lys Glu
    565                 570                 575

GCC AAA GAA AAA TTC CTC CAT GAA GTT GTT AAA ATG AGA GTG AAG CAG   1952
Ala Lys Glu Lys Phe Leu His Glu Val Val Lys Met Arg Val Lys Gln
580                 585                 590                 595

GAA GAG AAG CTA AAT GCT GCC TTG CAA GCC AAA CGC AGC CTA CAT CAG   2000
Glu Glu Lys Leu Asn Ala Ala Leu Gln Ala Lys Arg Ser Leu His Gln
                600                 605                 610

GAG CTG GAG TTC CTC AGA GTG GCA AAG AAG GAG AAA CTG AGA GAA GCA   2048
Glu Leu Glu Phe Leu Arg Val Ala Lys Lys Glu Lys Leu Arg Glu Ala
            615                 620                 625

ACG GAG GCA AAA CGC AAC TTA AGG AAA GAG ATT GAG CGT CTG AGA GCT   2096
Thr Glu Ala Lys Arg Asn Leu Arg Lys Glu Ile Glu Arg Leu Arg Ala
        630                 635                 640

GAG AAT GAG AAG AAA ATG AAG GAA GCA AAC GAG TCT CGG ATA CGG CTA   2144
Glu Asn Glu Lys Lys Met Lys Glu Ala Asn Glu Ser Arg Ile Arg Leu
    645                 650                 655

AAG AGG GAA CTG GAA CAA GCC AGG CAG ATC CGG GTT TGC GAC AAG GGT   2192
```

```
Lys Arg Glu Leu Glu Gln Ala Arg Gln Ile Arg Val Cys Asp Lys Gly
660             665                 670                 675

TGT GAA GCT GGC AGG CTT CGG GCC AAG TAC TCT GCC CAG ATT GAG GAC      2240
Cys Glu Ala Gly Arg Leu Arg Ala Lys Tyr Ser Ala Gln Ile Glu Asp
                680                 685                 690

CTA CAG GTT AAG CTT CAG CAT GCA GAG GCT GAC AGG GAG CAG CTC CGA      2288
Leu Gln Val Lys Leu Gln His Ala Glu Ala Asp Arg Glu Gln Leu Arg
            695                 700                 705

GCT GAC CTG ATG CAT GAG AGG GAG GCT CGA GAA CAC TTG GAA AAA GTA      2336
Ala Asp Leu Met His Glu Arg Glu Ala Arg Glu His Leu Glu Lys Val
        710                 715                 720

GTC AAG GAA CTT CAG GAA CAG CTG TGG CCT AAA TCA AGC AGT CAA TCC      2384
Val Lys Glu Leu Gln Glu Gln Leu Trp Pro Lys Ser Ser Ser Gln Ser
    725                 730                 735

AGC AGT GAA AAC ACA ACG AGC AAC ATG GAG AAT TAAACCACGT CGTCTAATAC    2437
Ser Ser Glu Asn Thr Thr Ser Asn Met Glu Asn
740                 745                 750

AACAGAATGA CATATATGCA CAGTAAGGGA GGATGGGTGG GGTACGTGTG TAAGTGCATG    2497

TGTGAGTAGT TGTGTCTTAA CACACAGATC TAGGAATATG GATTCTTATT AGTTGGAAGG    2557

CAAATGTTAC TCTTTATAAC AGAAGCACTG AATTACGCCT CTTTTTTTTT CCAATCCATA    2617

TAGCACAACA TCTTACTGTG CCTATAAAAC ACAAATGTGT TTATAAACAA AATACTTTTA    2677

AGTCCACAGC AAATTTTCTA CTGGCAAACT CCAAGCAAGC AGCATCCTCC AACTAGAATC    2737

AGAGTAAAAG GCAAGCATGG CAGTGTTTTC ATGTTGCCCT TCTGCCTGTC GGAACATTTT    2797

GGAATTTAAA AACAAACTTT TCTTATAAGC TATTTAAAGT AATTCATTAC ACAGACTTGG    2857

TATTAAAAAA AATTAACAAG ATTTTTTATA ACGAACCTTT AAAAGCAAAA CAAAAACCTT    2917

CGATGCACAA TTTTTACGAC TTGTTAAAGG CTTTGGGATT CTTACTGCAG AAGCCCTTTG    2977

GTGATGATGC CATTTCATTA GCAGTTTTTT TTAATCCTGT CCTGTGGTTG TATGAGAATT    3037

TCAGAGTGCT TTTCAAAGTT GATTTTTTTC CTTAGAAACA ATCACCTTCA TTTCCTGTCC    3097

TGAACACAAG AAGAAAGGAA GATGCAGGAC TGTAAGGGCG TGGGGAGGG CAGGAAGAGA    3157

AGATGGACGC TTTGGAATTA TAAACCCAGC CTTACAGACT TCAGTGTTTC AAATCACGCC    3217

ATGTTTTCTA AAGACGTCTT CATTAATCGA TGTGTTCAAA AGACTCACTT CATCCAAGAG    3277

CACTTCAGCT TTAGGAAAAG AAAGAAGGAA GTAAAGGAAG GAAATGGATG ACCTGTTAAG    3337

TTGGTTGAGA AATAAAGCAG AAGATGTGTT TTGAAGTCAT TCTGAAATCT TCGCGTCAGC    3397

TTTCAGTTCT CTGGAAAACT CATCTTTGTT GCACCATCTT ACCATAGAAT TCAGTATTTA    3457

CCTACTTCTA TTCTGAACTG TTTGTCAGGA TTTCTGTGCC CAAGGAGAGT GCAACACCGC    3517

ATTATTGGAT ACTACAGAAA AGAAAAACCA CGTTTTTGCT GCTGTGAATA AGCCTACATC    3577

TTTTTTAAAA GAAAAACTTC TGTTTTTAAG AATAGAAATT ACTTTAATTT TGGGATCCGA    3637

GCCGCAGCCC TGGAATAGAA ATGCAGCCTA CCATCACTCT GTCTTACTAC CATTGTTAGC    3697

GTCGTCGTTC ATTTTTTTTT AAACTGCACT TTGTCAGAAC CTCACTCTGC ATTTTATTCC    3757

ATATTTTGGA AGTTTACAAG TTCAGCATTC TCGATTCTGC TCTGCAGATG TTAAAATCAT    3817

CACCACCATT TTCCACCACG CGACACCTCG GCCGTCATTT CCATGTATGC AAAAGAAGAA    3877

CTCAGTGGGT ACAGAATGCT ACCAAATACA AAGGCAGCAG AGCAGCGTGC TGCTGGTTGG    3937

GTTTCACAGC TGCGCTGCAC GGCTGTGGCT GTCGAGGCTG GGAAGTGCTC AAATACAGTT    3997

GGTGCTTTAC TGAATGAGAG AGGAGTTATT TTCACCCACA CACACTCACC TCTGATACAC    4057

TCAAGCTCAG TGAAAAGTTG ATCTGGGGCT GCAGTTGTGC CTTCCAGCTC ATTTTTCCTC    4117
```

TCAGCATCTT CTATAGGCAA TGCTGACACT TTTTTTTTAA ACCTTAAAGA ATAAAAAG   4175

(2) INFORMATION FOR SEQ ID NO:2:

(i) SEQUENCE CHARACTERISTICS:
        (A) LENGTH: 750 amino acids
        (B) TYPE: amino acid
        (D) TOPOLOGY: linear (ii) MOLECULE TYPE: protein (ix) FEATURE:
        (A) NAME/KEY: Modified-site
        (B) LOCATION: 373
        (D) OTHER INFORMATION: /product= "OTHER"
            /note= "Xaa = Trp in c-ski;
            Xaa = Arg in v-ski"

(xi) SEQUENCE DESCRIPTION: SEQ ID NO:2:

```
Met Glu Thr Val Ser Arg Ser Ser Phe Gln Pro His Pro Gly Leu Gln
 1               5                  10                  15

Lys Thr Leu Glu Gln Phe His Leu Ser Ser Met Ser Ser Leu Gly Gly
             20                  25                  30

Pro Ala Ala Phe Ser Ala Arg Trp Ala Gln Glu Met Tyr Lys Lys Asp
         35                  40                  45

Asn Gly Lys Asp Pro Ala Glu Pro Val Leu His Leu Pro Pro Ile Gln
 50                  55                  60

Pro Pro Pro Val Met Pro Gly Pro Phe Phe Met Pro Ser Asp Arg Ser
 65                  70                  75                  80

Thr Glu Arg Cys Glu Thr Ile Leu Glu Gly Glu Thr Ile Ser Cys Phe
                 85                  90                  95

Val Val Gly Gly Glu Lys Arg Leu Cys Leu Pro Gln Ile Leu Asn Ser
                100                 105                 110

Val Leu Arg Asp Phe Ser Leu Gln Gln Ile Asn Ser Val Cys Asp Glu
            115                 120                 125

Leu His Ile Tyr Cys Ser Arg Cys Thr Ala Asp Gln Leu Glu Ile Leu
        130                 135                 140

Lys Val Met Gly Ile Leu Pro Phe Ser Ala Pro Ser Cys Gly Leu Ile
145                 150                 155                 160

Thr Lys Thr Asp Ala Glu Arg Leu Cys Asn Ala Leu Leu Tyr Gly Gly
                165                 170                 175

Thr Tyr Pro Pro His Cys Lys Lys Glu Phe Ser Ser Thr Ile Glu Leu
            180                 185                 190

Glu Leu Thr Glu Lys Ser Phe Lys Val Tyr His Glu Cys Phe Gly Lys
        195                 200                 205

Cys Lys Gly Leu Leu Val Pro Glu Leu Tyr Ser Asn Pro Ser Ala Ala
    210                 215                 220

Cys Ile Gln Cys Leu Asp Cys Arg Leu Met Tyr Pro Pro His Lys Phe
225                 230                 235                 240

Val Val His Ser His Lys Ser Leu Glu Asn Arg Thr Cys His Trp Gly
                245                 250                 255

Phe Asp Ser Ala Asn Trp Arg Ser Tyr Ile Leu Leu Ser Gln Asp Tyr
            260                 265                 270

Thr Gly Lys Glu Glu Lys Ala Arg Leu Gly Leu Leu Asp Glu Met
        275                 280                 285

Lys Glu Lys Phe Asp Tyr Asn Asn Lys Tyr Lys Arg Lys Ala Pro Arg
    290                 295                 300

Asn Arg Glu Ser Pro Arg Val Gln Leu Arg Arg Thr Lys Met Phe Lys
```

-continued

```
305                 310                 315                 320
Thr Met Leu Trp Asp Pro Ala Gly Gly Ser Ala Val Leu Gln Arg Gln
                325                 330                 335
Pro Asp Gly Asn Glu Val Pro Ser Asp Pro Ala Ser Lys Lys Thr
                340                 345                 350
Lys Ile Asp Asp Ser Ala Ser Gln Ser Pro Ala Ser Thr Glu Lys Glu
                355                 360                 365
Lys Gln Ser Ser Xaa Leu Arg Ser Leu Ser Ser Ser Asn Lys Ser
                370                 375                 380
Ile Gly Cys Val His Pro Arg Gln Arg Leu Ser Ala Phe Arg Pro Trp
385                 390                 395                 400
Ser Pro Ala Val Ser Ala Asn Glu Lys Glu Leu Ser Thr His Leu Pro
                405                 410                 415
Ala Leu Ile Arg Asp Ser Ser Phe Tyr Ser Tyr Lys Ser Phe Glu Asn
                420                 425                 430
Ala Val Ala Pro Asn Val Ala Leu Ala Pro Pro Ala Gln Gln Lys Val
                435                 440                 445
Val Ser Asn Pro Pro Cys Ala Thr Val Val Ser Arg Ser Ser Glu Pro
    450                 455                 460
Pro Ser Ser Ala Ala Gln Pro Arg Lys Arg Lys His Ala Ala Glu Thr
465                 470                 475                 480
Pro Ala Val Pro Glu Pro Val Ala Thr Val Thr Ala Pro Glu Glu Asp
                485                 490                 495
Lys Glu Ser Glu Ala Glu Ile Glu Val Glu Thr Arg Glu Glu Phe Thr
                500                 505                 510
Ser Ser Leu Ser Ser Leu Ser Ser Pro Ser Phe Thr Ser Ser Ser Ser
                515                 520                 525
Ala Lys Asp Met Ser Ser Pro Gly Met Gln Ala Pro Val Pro Val Asn
                530                 535                 540
Ser Ser Tyr Glu Val Ala Ala His Ser Asp Ser His Ser Ser Gly Leu
545                 550                 555                 560
Glu Ala Glu Leu Glu His Leu Arg Gln Ala Leu Asp Ser Gly Leu Asp
                565                 570                 575
Thr Lys Glu Ala Lys Glu Lys Phe Leu His Glu Val Val Lys Met Arg
                580                 585                 590
Val Lys Gln Glu Glu Lys Leu Asn Ala Ala Leu Gln Ala Lys Arg Ser
                595                 600                 605
Leu His Gln Glu Leu Glu Phe Leu Arg Val Ala Lys Lys Glu Lys Leu
    610                 615                 620
Arg Glu Ala Thr Glu Ala Lys Arg Asn Leu Arg Lys Glu Ile Glu Arg
625                 630                 635                 640
Leu Arg Ala Glu Asn Glu Lys Lys Met Lys Glu Ala Asn Glu Ser Arg
                645                 650                 655
Ile Arg Leu Lys Arg Glu Leu Glu Gln Ala Arg Gln Ile Arg Val Cys
                660                 665                 670
Asp Lys Gly Cys Glu Ala Gly Arg Leu Arg Ala Lys Tyr Ser Ala Gln
                675                 680                 685
Ile Glu Asp Leu Gln Val Lys Leu Gln His Ala Glu Ala Asp Arg Glu
                690                 695                 700
Gln Leu Arg Ala Asp Leu Met His Glu Arg Glu Ala Arg Glu His Leu
705                 710                 715                 720
Glu Lys Val Val Lys Glu Leu Gln Glu Gln Leu Trp Pro Lys Ser Ser
                725                 730                 735
```

```
            Ser Gln Ser Ser Ser Glu Asn Thr Thr Ser Asn Met Glu Asn
                    740                 745                 750

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..26
        (D) OTHER INFORMATION: /note= "positions 633 to 658 from
            the p19 region of gag of avian
            leukosis virus"

(xi) SEQUENCE DESCRIPTION: SEQ ID NO:3:

GAGAGGAACA GGTTACATCT GAGCAA                                          26

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..25
        (D) OTHER INFORMATION: /note= "positions 218 to 242 of c-ski"

(xi) SEQUENCE DESCRIPTION: SEQ ID NO:4:

CCTTGGAACA GTTTCATCTG AGCTC                                           25
```